(12) United States Patent
Kotov

(10) Patent No.: US 9,534,213 B2
(45) Date of Patent: Jan. 3, 2017

(54) SPONTANEOUSLY FORMED TERMINAL SUPRAPARTICLES HAVING NANOPARTICLES FOR PROTEIN STABILIZATION

(71) Applicant: THE REGENTS OF THE UNIVERSITY OF MICHIGAN, Ann Arbor, MI (US)

(72) Inventor: Nicholas A. Kotov, Ypsilanti, MI (US)

(73) Assignee: The Regents Of The University Of Michigan, Ann Arbor, MI (US)

( * ) Notice: Subject to any disclaimer, the term of this patent is extended or adjusted under 35 U.S.C. 154(b) by 0 days.

(21) Appl. No.: 14/635,347

(22) Filed: Mar. 2, 2015

(65) Prior Publication Data

US 2015/0252350 A1 Sep. 10, 2015

Related U.S. Application Data

(60) Provisional application No. 61/947,592, filed on Mar. 4, 2014.

(51) Int. Cl.
*C07K 14/00* (2006.01)
*C12N 9/96* (2006.01)

(52) U.S. Cl.
CPC ....................................... *C12N 9/96* (2013.01)

(58) Field of Classification Search
None
See application file for complete search history.

(56) References Cited

U.S. PATENT DOCUMENTS

| 8,080,183 | B2 | 12/2011 | Kotov et al. |
| 8,460,907 | B2 | 6/2013 | Walker et al. |
| 2009/0258076 | A1* | 10/2009 | Cheon ................. A61K 41/0042 424/491 |
| 2011/0318297 | A1 | 12/2011 | Lu et al. |
| 2013/0101669 | A1 | 4/2013 | Appleford et al. |

FOREIGN PATENT DOCUMENTS

WO 2013006762 A2 1/2013

OTHER PUBLICATIONS

Ipe, Binil Itty., Niemeyer, Christof M. Nanohybrids Composed of Quantum Dots and Cytochrome P450 as Photocatalysts. Angrew Chem. Int. Ed. 2006, 45, 504-507.
Ge, Jun, Lei, Jiandu, Zare, Richard N. Protein-Inorganic Hybrid Nanoflowers. Nature Nanotechnology, vol. 7, Jul. 2012.pp. 428-432.
Wei, Wei et al. Construction of Robust Enzyme Nanocapsules for Effective Organophosphate Decontamination, Detoxification,and Protection. Advanced Materials, vol. 25: Issues 15, pp. 2212-2218. Apr. 18, 2013. (abstract only).
Zeng, Jie, Xia, Younan. Hybrid Nanomaterials: Not Just a Pretty Flower. Nature Nanotechnology 7, 415-416 (2012).
Zhang et al., "Simulations and analysis of self-assembly of CdTe nanoparticles into wires and sheets," Nano Lett. 7, 1670-1675 (2007).

* cited by examiner

*Primary Examiner* — Anand Desai
(74) *Attorney, Agent, or Firm* — Harness, Dickey & Pierce, PLC

(57) ABSTRACT

Supraparticle nanoassemblies are provided that comprise nanoparticle species and protein species, as well as methods for making such assemblies. A supraparticle may comprise a nanoparticle species with a first charge and an average particle size diameter of ≥about 1 nm to ≤about 100 nm. The supraparticle also comprises a protein species. The nanoparticle species and the protein species have the same charge and are assembled together without any intramolecular chemical bonding to form the supraparticle. The supraparticle may be a substantially round particle. In certain other aspects, a photoreactive supraparticle is provided, where the nanoparticle is reactive to energy or electromagnetic radiation, which in the presence of such energy or radiation enhances reactivity of the protein species in the supraparticle.

17 Claims, 26 Drawing Sheets

Figures 1A, 1B, 1C, 1D, 1E, 1F:
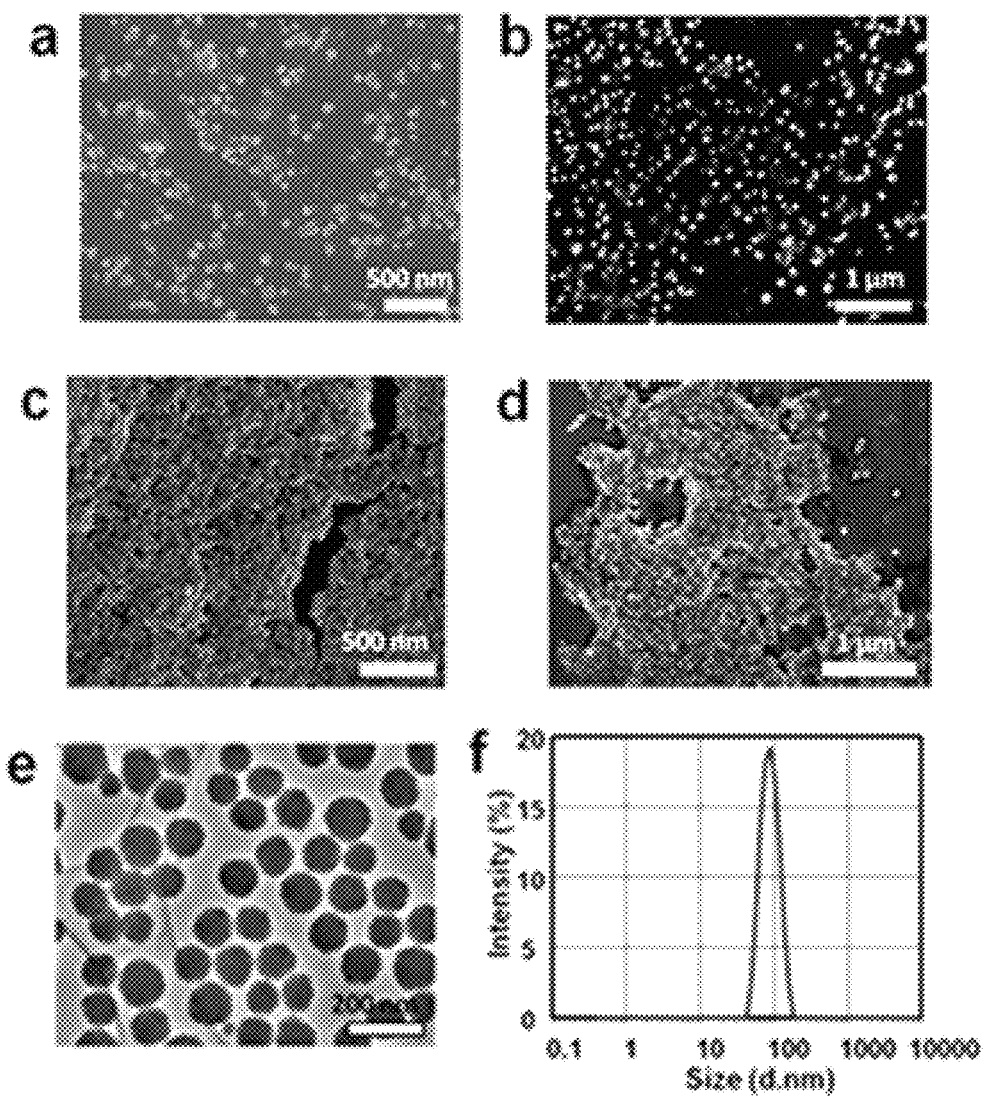

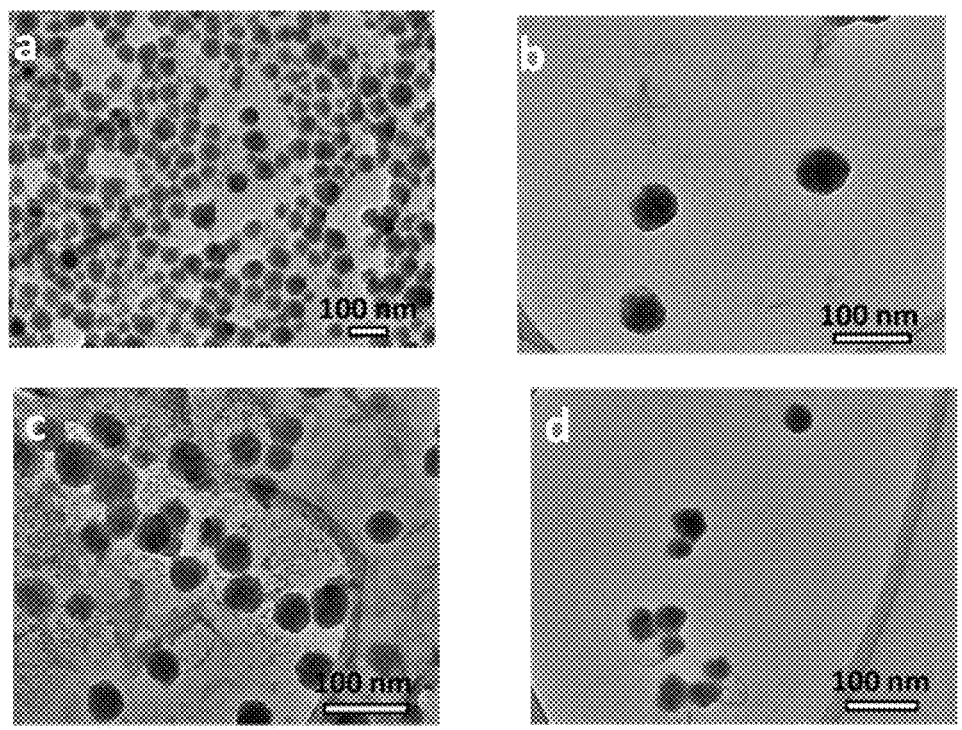
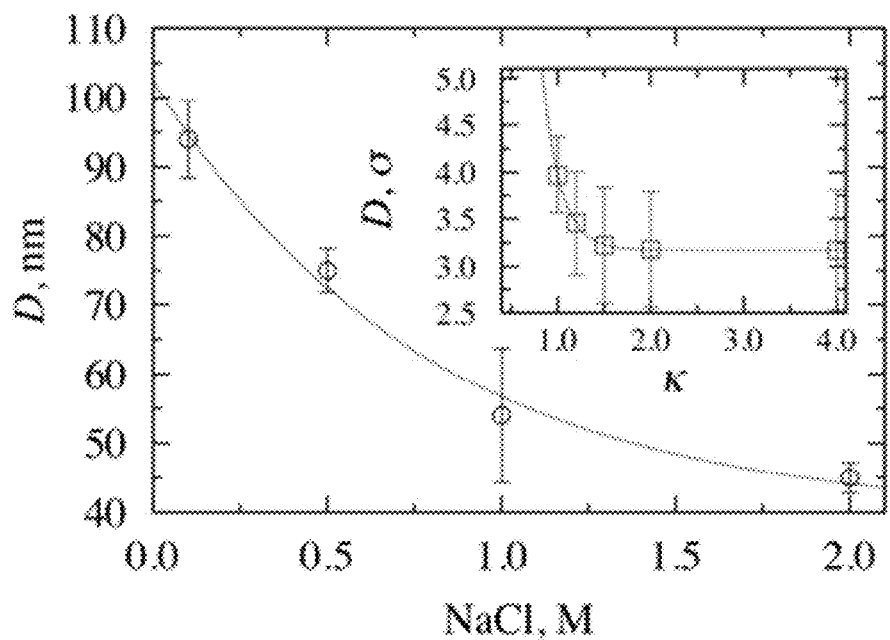
Figures 3A-3E

SPONTANEOUSLY FORMED TERMINAL SUPRAPARTICLES HAVING NANOPARTICLES FOR PROTEIN STABILIZATION

CROSS-REFERENCE TO RELATED APPLICATIONS

This application claims the benefit of U.S. Provisional Application No. 61/947,592, filed on Mar. 4, 2014. The entire disclosure of the above application is incorporated herein by reference.

GOVERNMENT RIGHTS

This invention is made with government support under CBET0932823 awarded by the National Science Foundation. The Government has certain rights in the invention.

FIELD

The present disclosure relates to spontaneously formed terminal assemblies made from nanoparticles and proteins that form supraparticle assemblies to provide superior protein (e.g., enzyme) stabilization.

BACKGROUND

This section provides background information related to the present disclosure which is not necessarily prior art.

Various biological substances can be used in industrial and engineered applications. For example, certain proteins, such as enzymes, are biological catalysts that are frequently used to increase rates of chemical reactions by lowering the energy barrier for them to occur. Enzymes are powerful catalysts because they are highly specific to certain target compounds, operate at ambient temperatures and pressures, and are environmentally friendly. Use of enzymes decreases consumption of energy, while enzymes demonstrate a high degree of utility due to their speed of reaction, specificity for certain analytes, ability to be engineered and chemically modified, and environmentally and bio-friendly processes. Thus, enzymes are used in many industries including food processing, detergents and cleaning products, pulp and paper, textiles and leather, pharmaceuticals, cosmetics, biotechnology, clinical diagnostics, wastewater treatment, fuel production, including bioethanol and biofuel production, and decontamination of chemical agents, by way of non-limiting example.

However, stabilization of proteins and, in particular enzymes, is important to guard against spontaneous loss of biological activity. A major impediment to widespread use of enzymes and other proteins or biological substances is an inability to sufficiently stabilize their tertiary structure in harsh environmental conditions. Many biological substances, including enzymes and proteins, are sensitive to extreme environmental conditions, such as heat or high temperatures, extreme pressure, extreme high or low pH, ionic strength, salinity, exposure to certain chemical agents or solvents, and the like. When proteins or enzymes are exposed to such harsh environmental conditions, the proteins can be easily denatured or rendered inactive by undergoing different denaturizing reactions, which entails loss of activity due to unfolding of the protein structure. As a result, use of proteins, like enzymes, for large-scale commercial use, especially for continuous use, is extremely limited. This sensitivity of biological substances, like proteins, represents a tremendous problem in chemical and biochemical industries. Thus, it would be desirable to develop methods for stabilizing proteins or enzymes to retain catalytic or other activity in various environments, including during manufacturing and production, storage, and use in various commercial or industrial applications.

SUMMARY

This section provides a general summary of the disclosure, and is not a comprehensive disclosure of its full scope or all of its features.

In various aspects, the present disclosure provides assemblies of nanoparticle species and protein species and methods for making such assemblies. In certain variations, the present disclosure provides a supraparticle that comprises a nanoparticle species having a surface with a first charge. The nanoparticle species has an average particle size diameter of greater than or equal to about 1 nm to less than or equal to about 100 nm. The supraparticle also comprises a protein species having a second charge that is the same as the first charge. The nanoparticle species and the protein species (respectively having the same charge) are assembled together without any intramolecular chemical bonding to form the supraparticle.

In other variations, the present disclosure contemplates a supraparticle that comprises a nanoparticle species having a surface with a first charge and an average particle size diameter of greater than or equal to about 1 nm to less than or equal to about 100 nm. The supraparticle also comprises a protein species having a second charge that is the same as the first charge. The nanoparticle species and the protein species are assembled together without any intramolecular chemical bonding to form the supraparticle having a substantially round shape.

In yet other aspects, the present disclosure provides a photoreactive supraparticle that comprises a nanoparticle species having a surface with a first charge. The nanoparticle species has an average particle size diameter of greater than or equal to about 1 nm to less than or equal to about 100 nm. Further, the nanoparticle species is reactive to electromagnetic radiation. A protein species is also part of the supraparticle. The protein species has a second charge that is the same as the first charge. The nanoparticle species and the protein species are assembled together without any intramolecular chemical bonding to form the supraparticle. Furthermore, in the presence of electromagnetic radiation, the protein species in the supraparticle has a reactivity that is at least 100% greater than a comparative reactivity of the protein species in the absence of the electromagnetic radiation.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 1A-1F. Assembly of CdTe NPs and CytC. FIGS. 1A-1D show SEM images of CdTe/CytC assemblies with molar ratio of CdTe:CytC as 1:1 (FIG. 1A), 2:1 (FIG. 1B), 6:1 (FIG. 1C), and 1:6 (FIG. 1D). FIG. 1E shows a TEM image of CdTe/CytC SPs. FIG. 1F shows size distribution of the self-assembled SPs by dynamic light scattering.

Figures 2A, 2B:
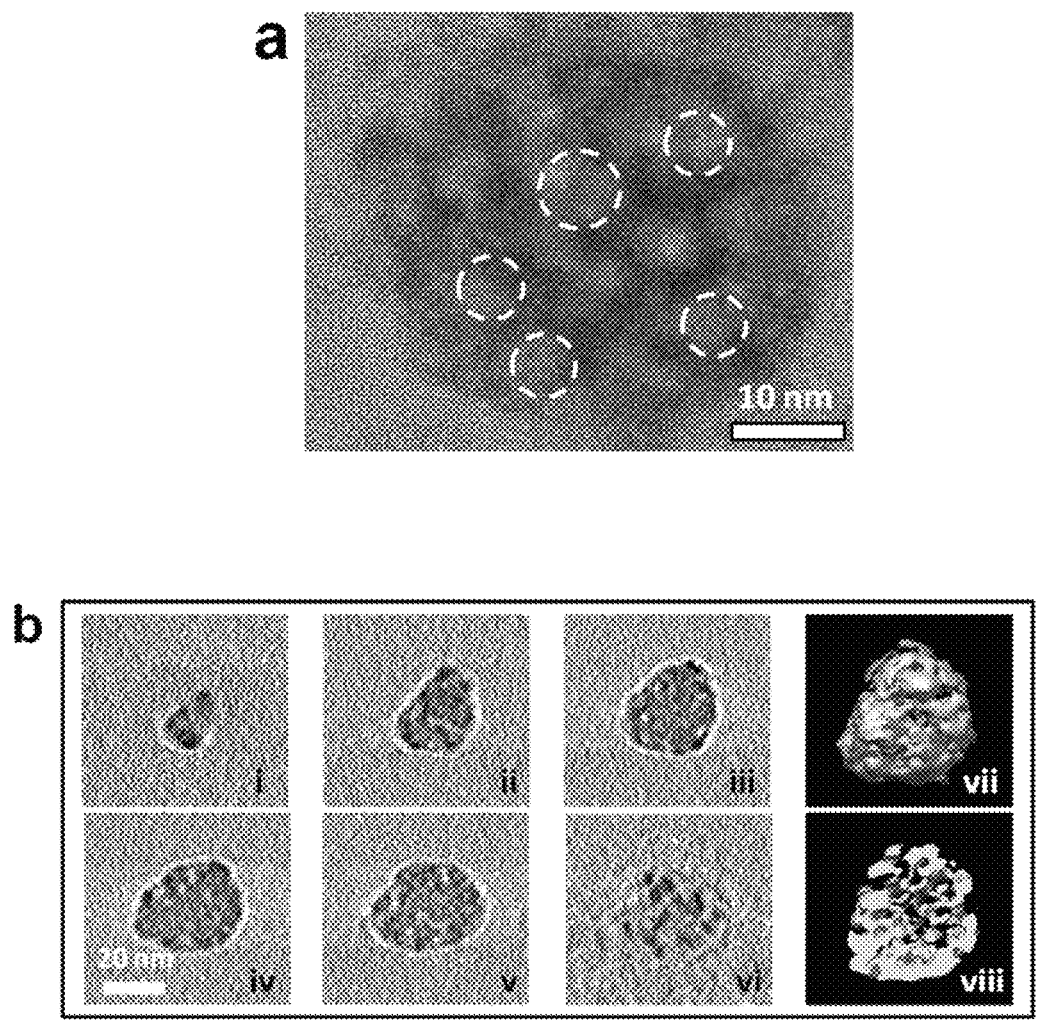
Figure 2C:
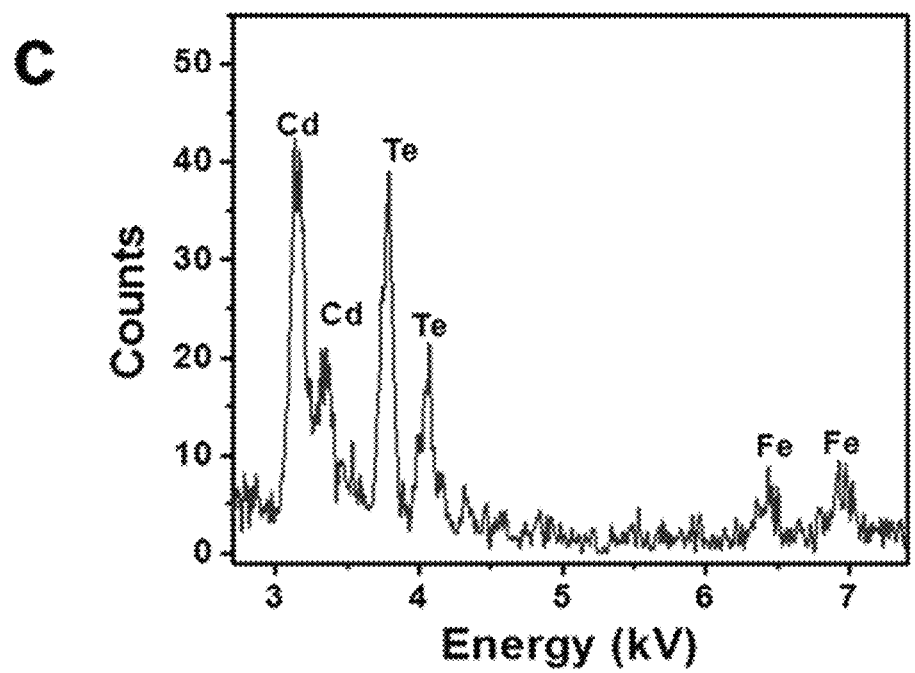
Figure 2D:
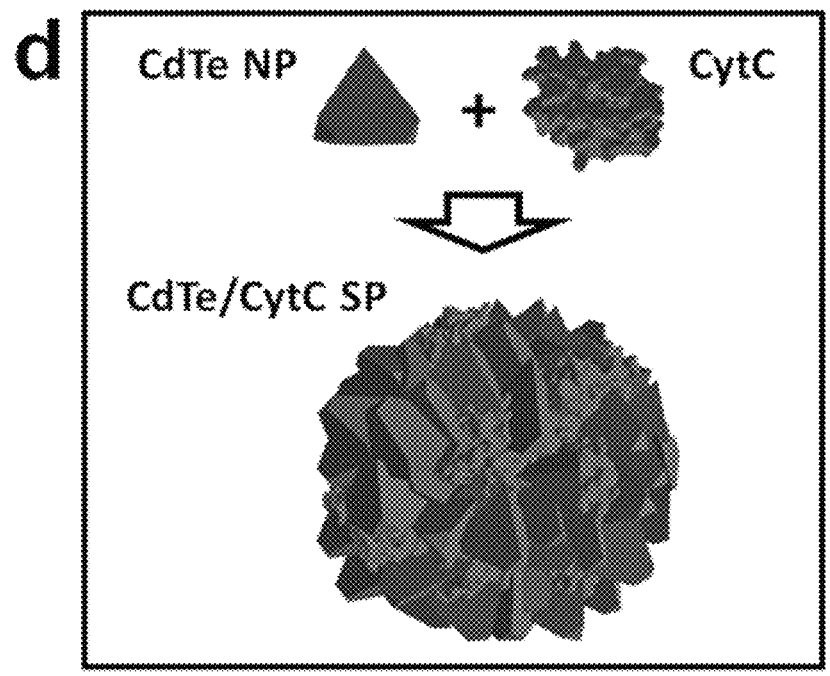
Figures 2E, 2F:
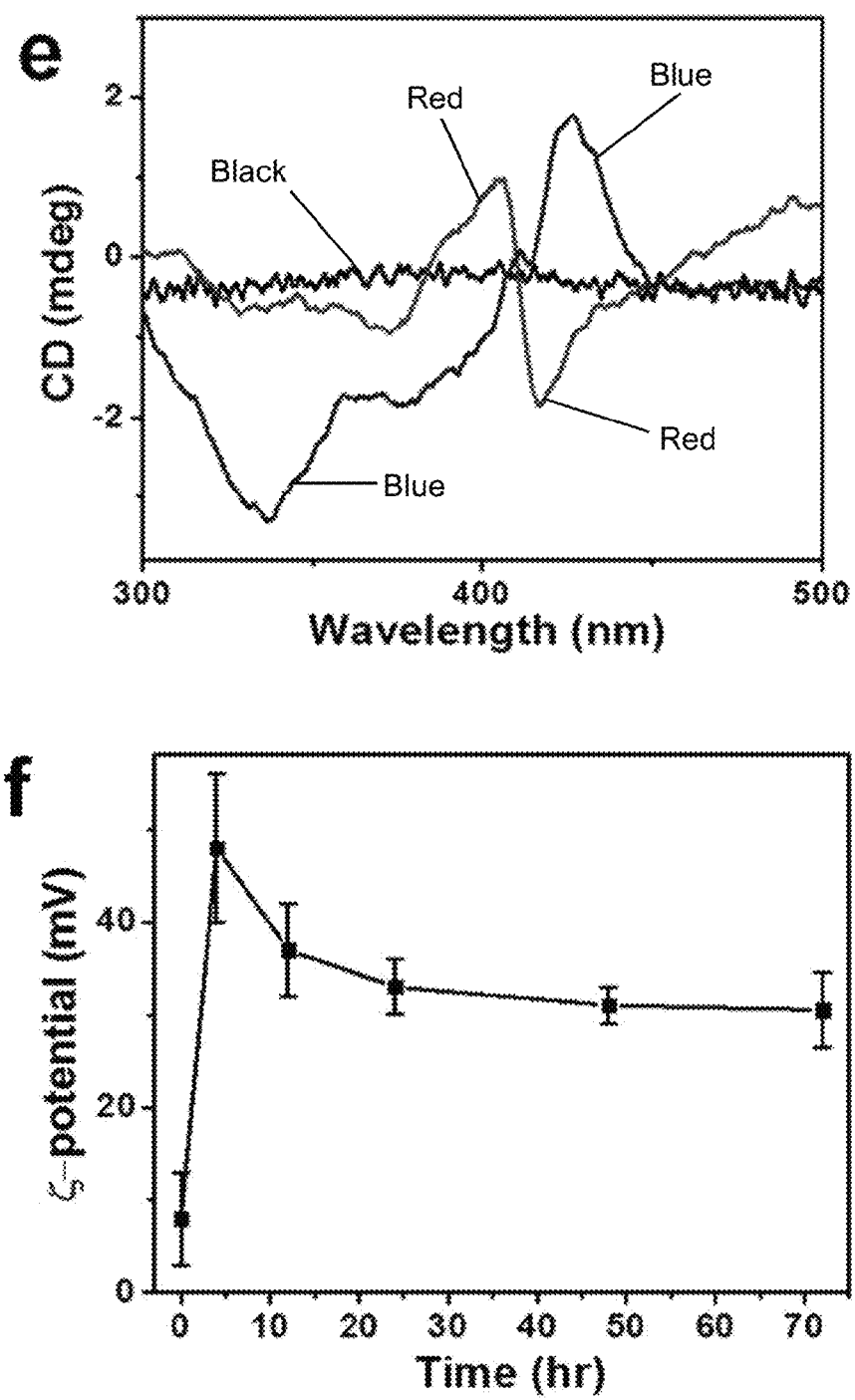

FIGS. 2A-2F. Structural Characterization of CdTe/CytC supraparticles. FIG. 2A shows HRTEM image of the SP. Lighter areas correspond to CytC-rich phase (white-dashed circles) while the darker ones correspond to CdTe-rich phase. FIG. 2B shows TEM tomography images of CdTe/CytC SP: X-Y slices (i-vi) of the SP, shown in every 4.8 nm through the volume. 3D surface reconstruction (vii) and cross-section (viii) of the SP are also shown. FIG. 2C show XEDS spectrum for an SP in FIG. 2A. FIG. 2D shows schematics of the CdTe-CytC SPs. FIG. 2E shows CD spectra for CytC (red, 6 μM), CdTe NPs (black, 6 μM), 1:1 mixture of CdTe/CytC after 72 (blue) hrs. FIG. 2F shows ξ-potential values for the assembly of CdTe NPs with CytC at different time intervals.

Figure 3F:
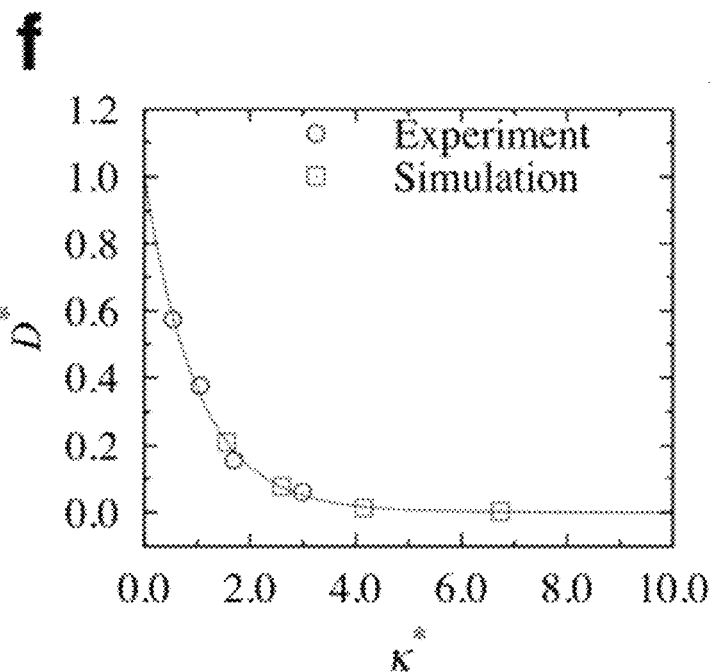
Figure 3G:
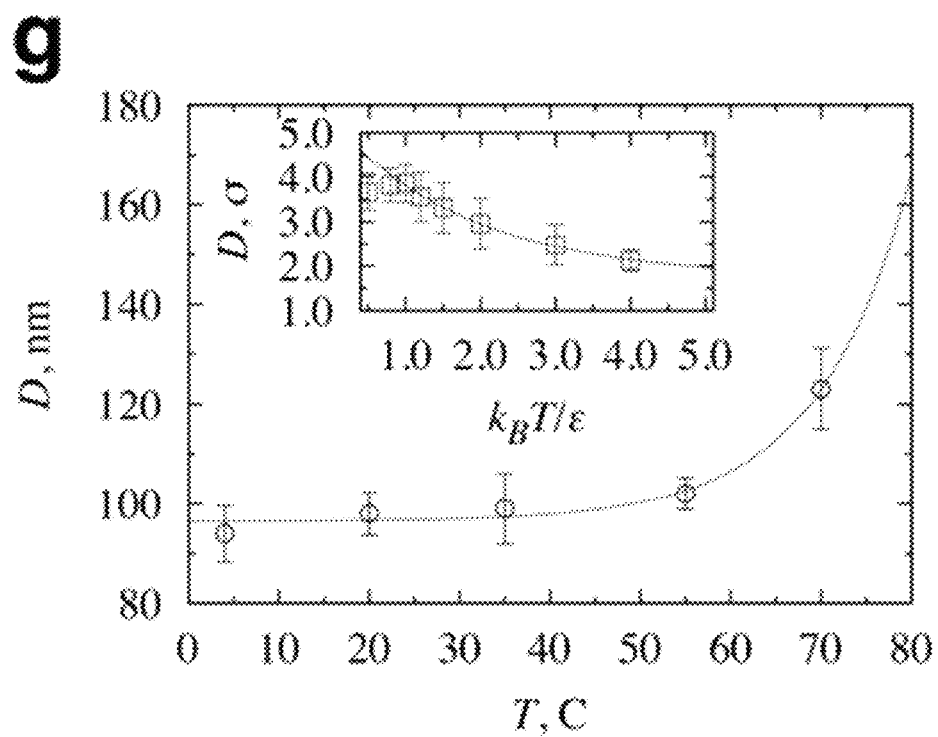
Figure 3H:
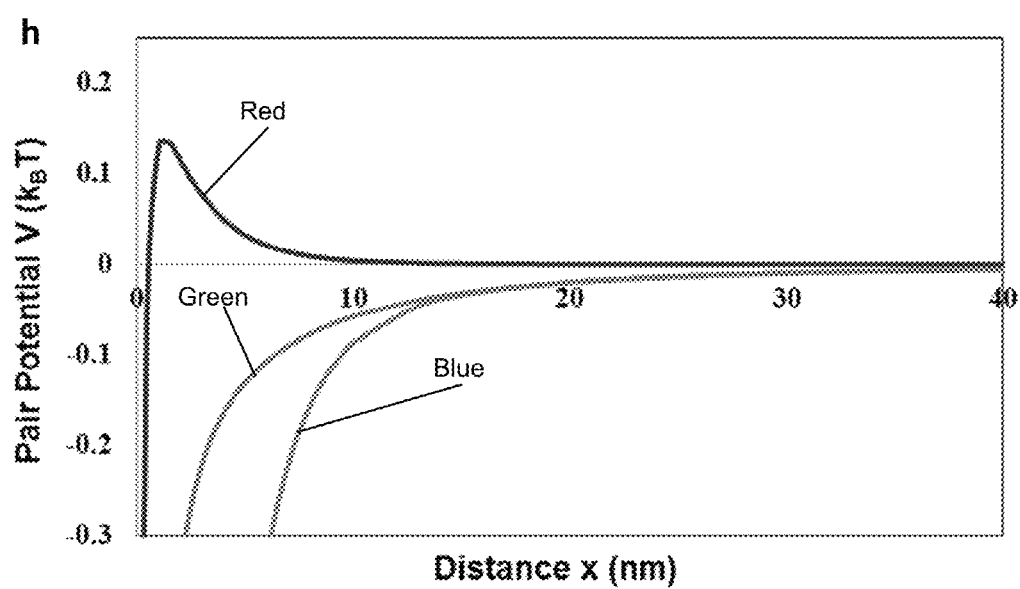

FIGS. 3A-3H. Simulated and experimental dependences of SP diameters on media parameters. FIGS. 3A-3D show TEM images of SPs made in the solutions with (FIG. 3A) 0.1 M, (FIG. 3B) 0.5 M, (FIG. 3C) 1.0 M and (FIG. 3D) 2.0 M of NaCl. FIG. 3E shows dependence of SP diameters on the NaCl concentration of NaCl and on inverse screening length in simulation. FIG. 3F shows experimental and simulated data fitted against decaying laws, i.e., f(x) about exp(-x), and plotted against dimensionless inverse screening length ($\kappa^*$) and normalized diameters ($D^*$). FIG. 3G shows temperature dependence of the SP diameters in experiment and in simulation (inset). FIG. 3H shows pair potential between CdTe NPs and CytC according to DLVO and E-DLVO theories: $V_{DLVO}=V_{vdW}+V_{DL}$ (red); $V_{E-DLVO1}=V_{vdW}+V_{DL}+V_{DP}+V_{Q-DP}$ (green); $V_{E-DLVO2}=V_{vdW}+V_{DL}+V_{DP}+V_{Q-DP}+V_{HB}$ (blue).

Figures 4A, 4B:
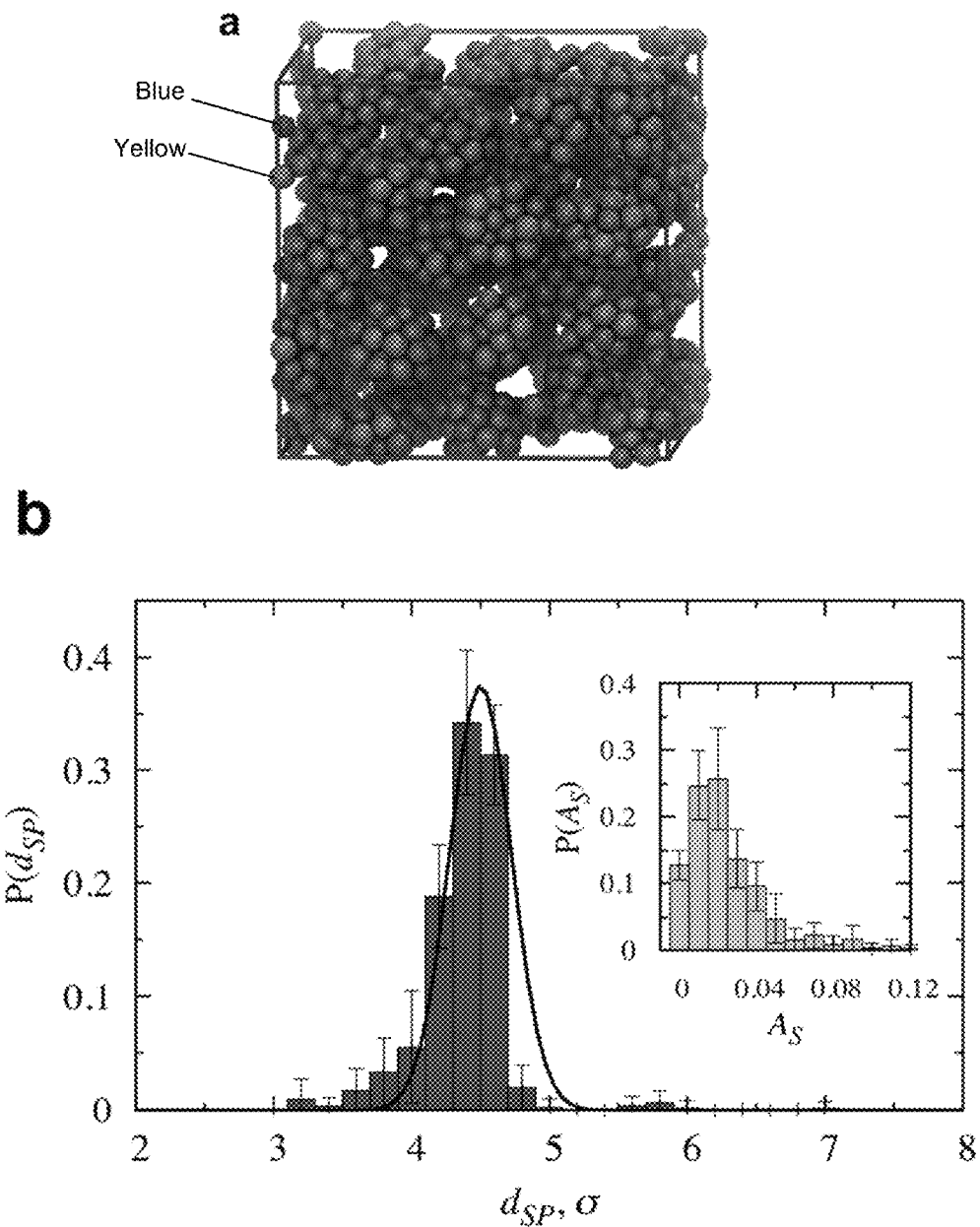
Figures 4C, 4D, 4E:
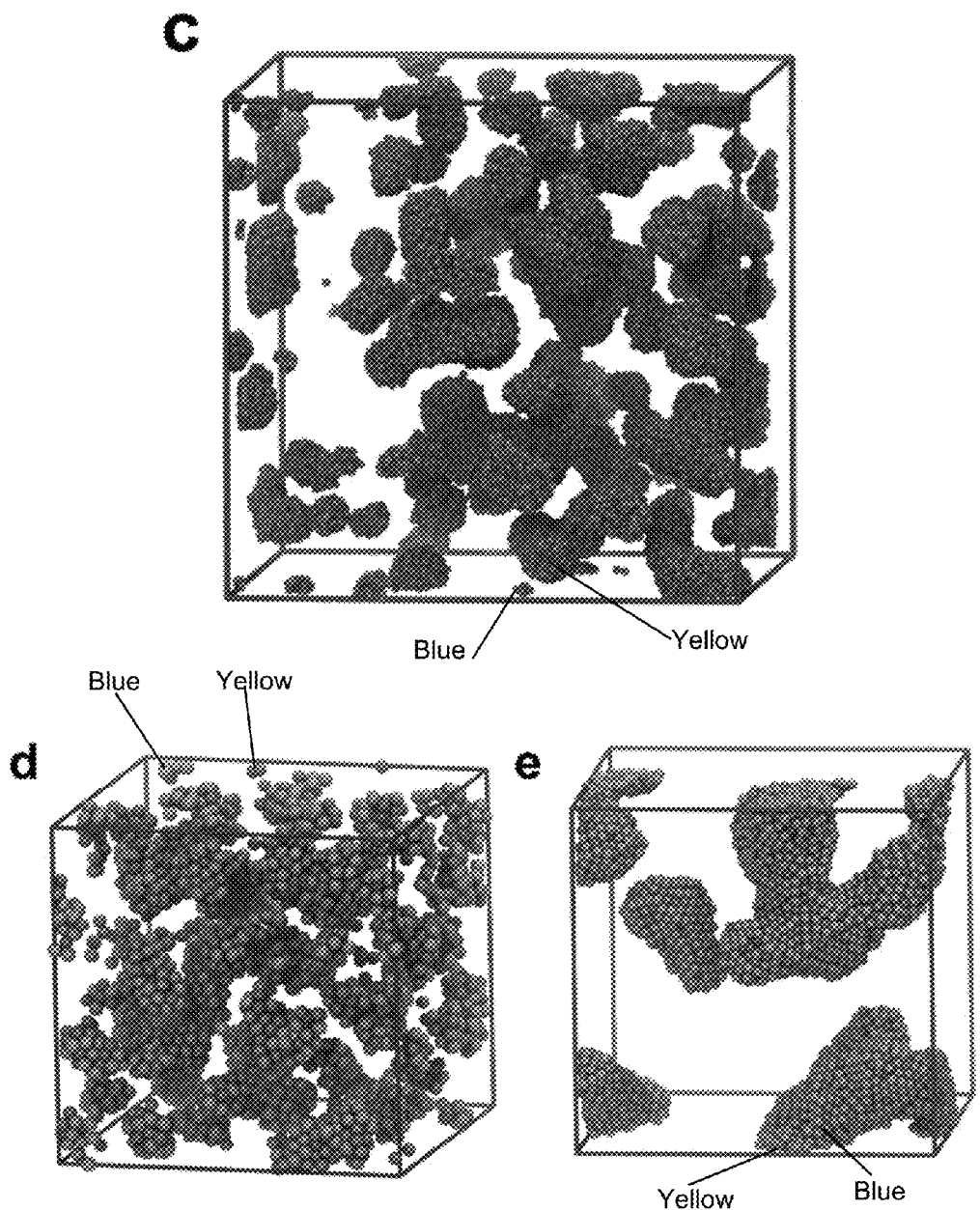

FIGS. 4A-4E. Simulation Results. FIG. 4A shows spherical assemblies formed by a mixture of 1000 NPs (yellow) and 1000 CytC units (blue) at $\rho\sigma^3=0.25$. FIG. 4B shows distribution of SP sizes and of the asphericity parameter ($A_S$) (inset) of a system composed of 8000 NPs and 8000 CytC units (see also, FIG. 18A). $A_S=0$ corresponds to perfect spheres. Error bars are obtained from 10 equilibrated, independent configurations separated by intervals of 2000τ. FIG. 4C shows a snapshot of a system identical to FIG. 4A, but without the inter-SP charge-charge repulsion renormalization. FIGS. 4D-4E show snapshots of mixtures with NP/CytC molar ratios of 2:1 and 6:1, respectively. The images in FIG. 4A and FIGS. 4C-4E are generated using the software VMD.

Figure 5A:
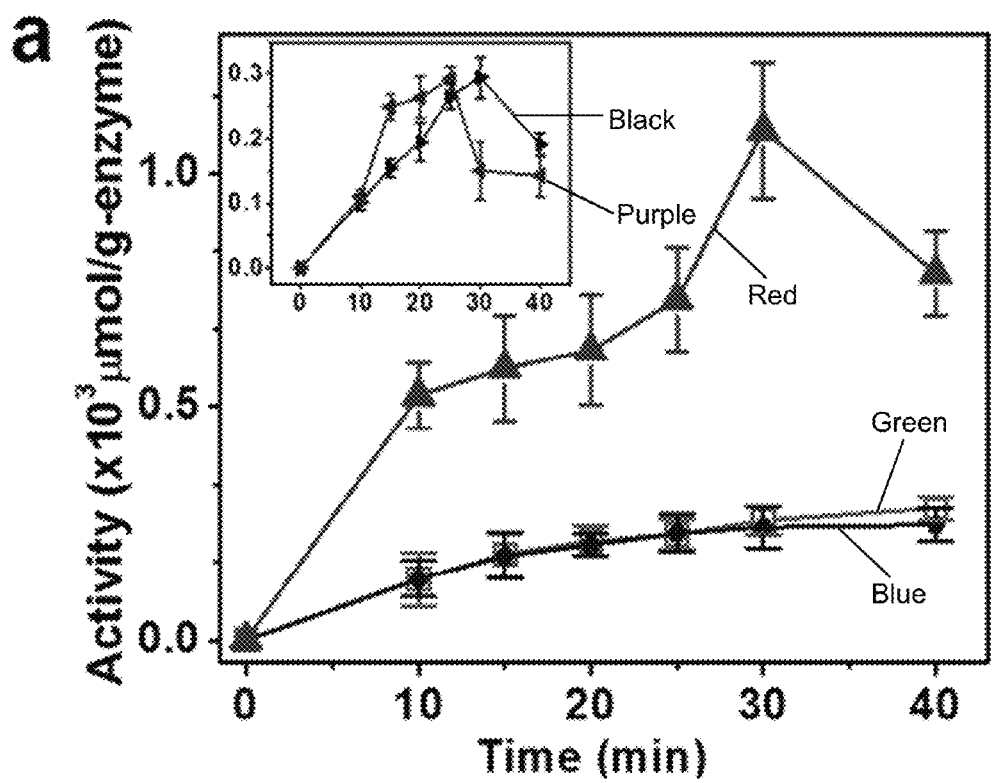
Figure 5B:
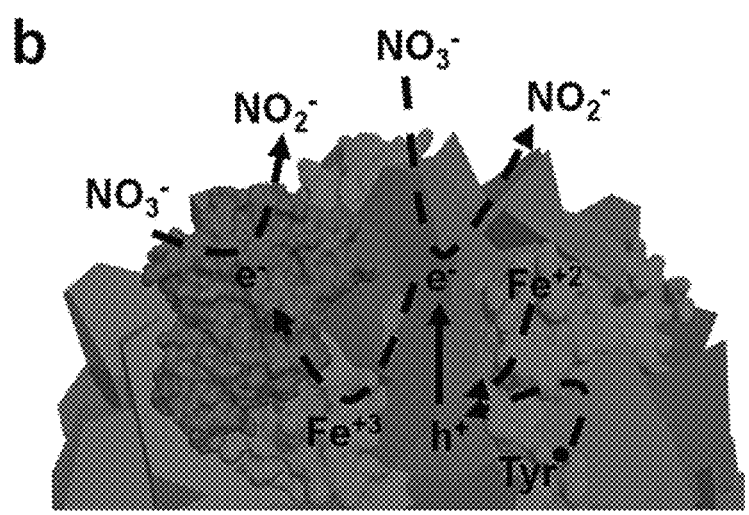

FIGS. 5A-5D. Functional Integration-Multicomponent SPs with Photoenzymatic Activity. FIG. 5A shows formation of nitrite for SP-NADPH-NRed (red) excited at 470 nm and for NADPH-NRed (green) and SP-NADPH-NRed in dark (blue). Inset: Formation of nitrite for NADPH-NRed being excited at 470 nm in presence of only one of SP components: either CdTe NPs (black) or CytC (purple) when no hybrid SP is formed. FIG. 5B shows schematics of the reactions upon the photo-excitation of SP-NADPH-NRed. Nitrate reductase is represented as a surface model from PyMol software, PDB entry is 2BIH. TEM images of FIG. 5C, SP-NADPH-NRed after 20 min, and FIG. 5D, after 40 min of the of photoenzymatic reaction, are also shown. Scale bars are 100 nm.

Figure 6:
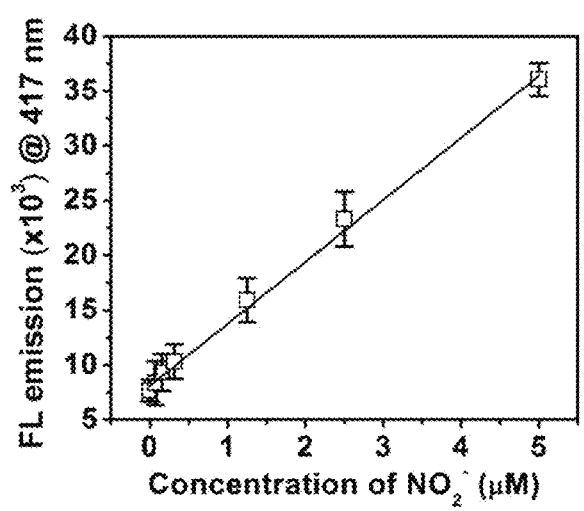

FIG. 6. A standard plot of the different concentrations of $NO_2^-$.

Figures 7A, 7B, 7C:
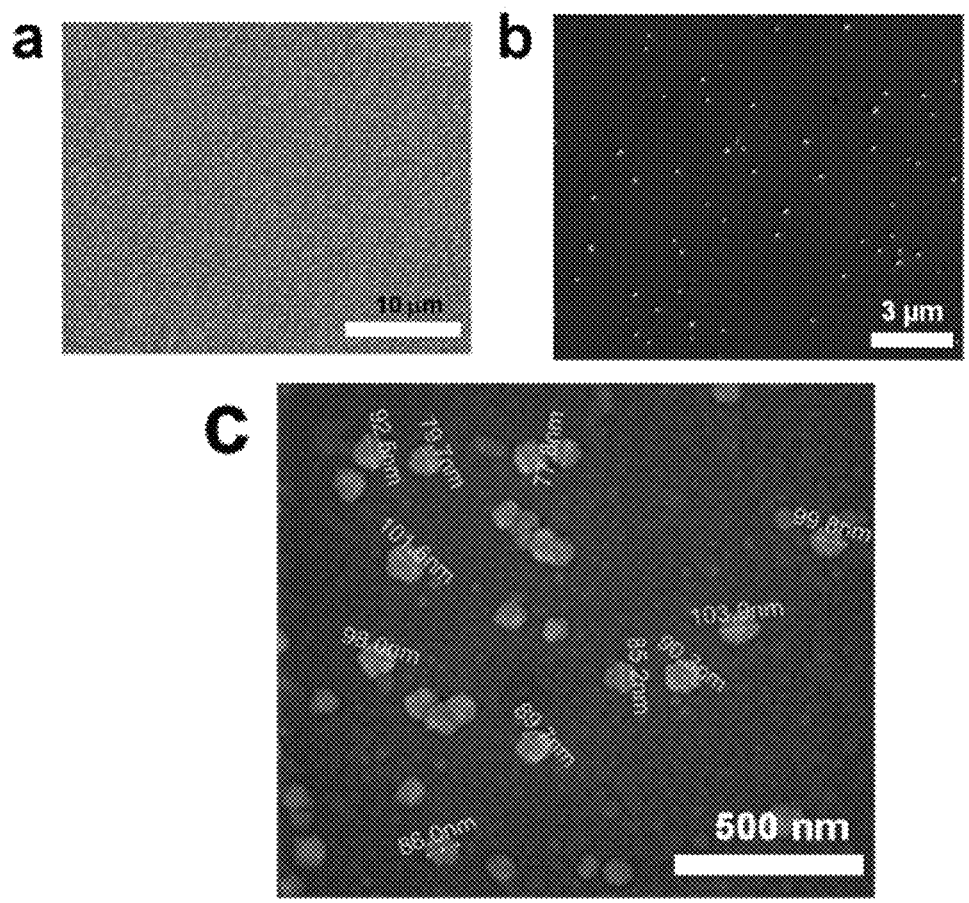

FIGS. 7A-7C. Scanning electron microscopy (SEM) images of SPs with 1:1 CdTe/CytC ratio after 72 hours of assembly.

Figure 8:
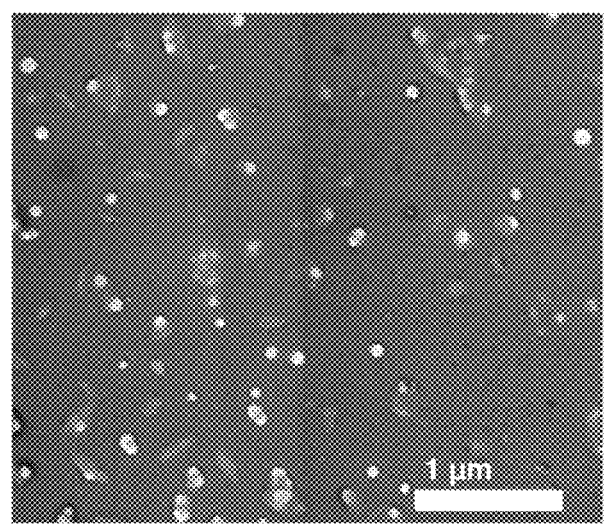

FIG. 8. SEM images of assembly of SPs with 1:2 CdTe/CytC ratio after 72 hours of assembly.

Figures 9A, 9B:
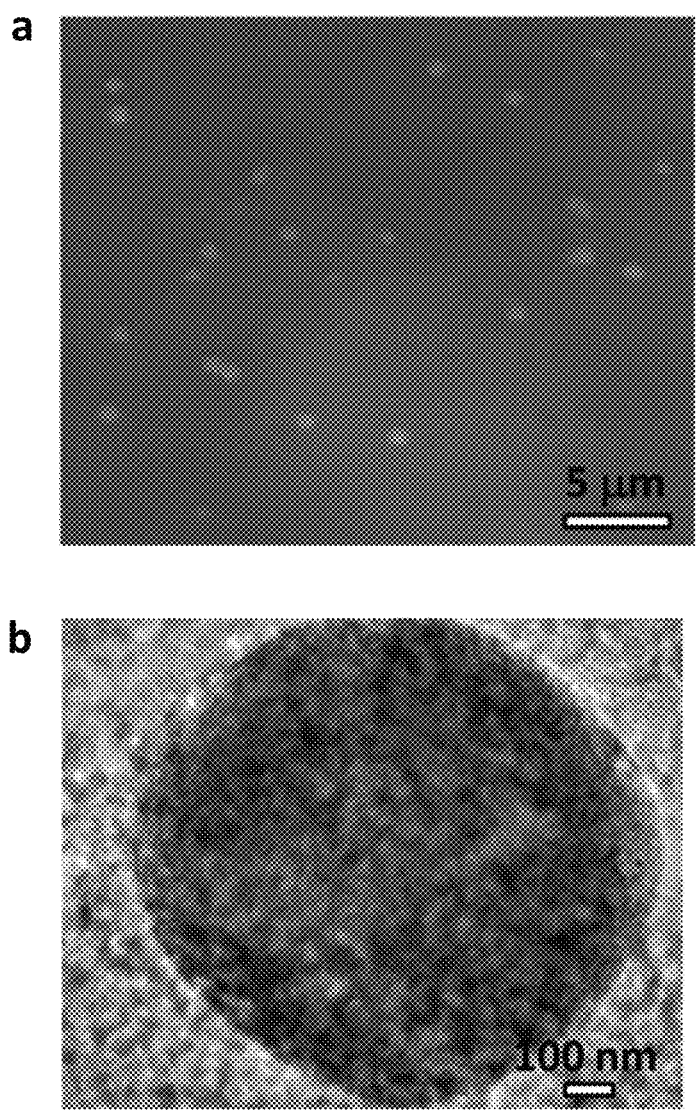

FIGS. 9A-9B. FIG. 9A is an SEM and FIG. 9B is a TEM image of SPs assembled from 13.5 nm CdTe NPs and CytC under the same conditions as those in FIGS. 1A-1F and 2A-2F.

Figure 10:
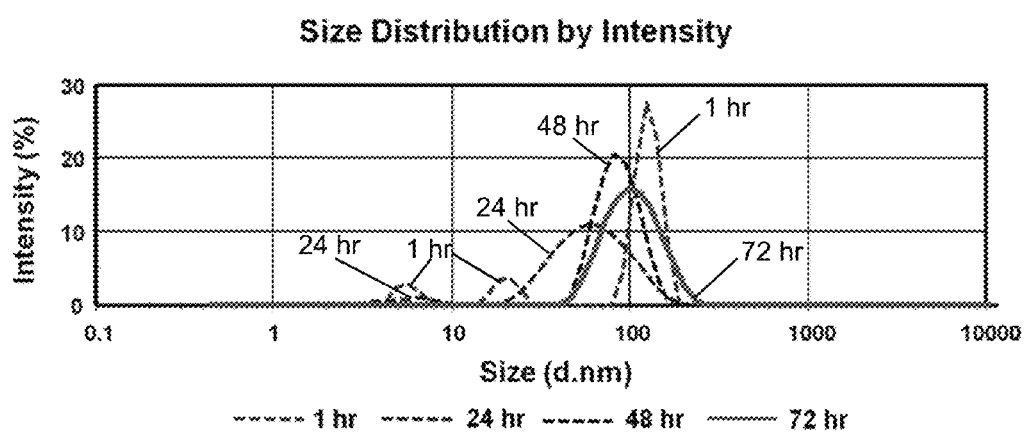

FIG. 10. DLS curves for particle size distribution for different times of self-assembly process between CdTe and CytC (1:1 CdTe:CytC ratio). A wider size distribution occurs in the early stages (24 hours) indicative of the gradual emergence of SP with an equilibrium diameter.

Figures 11A, 11B, 11C:
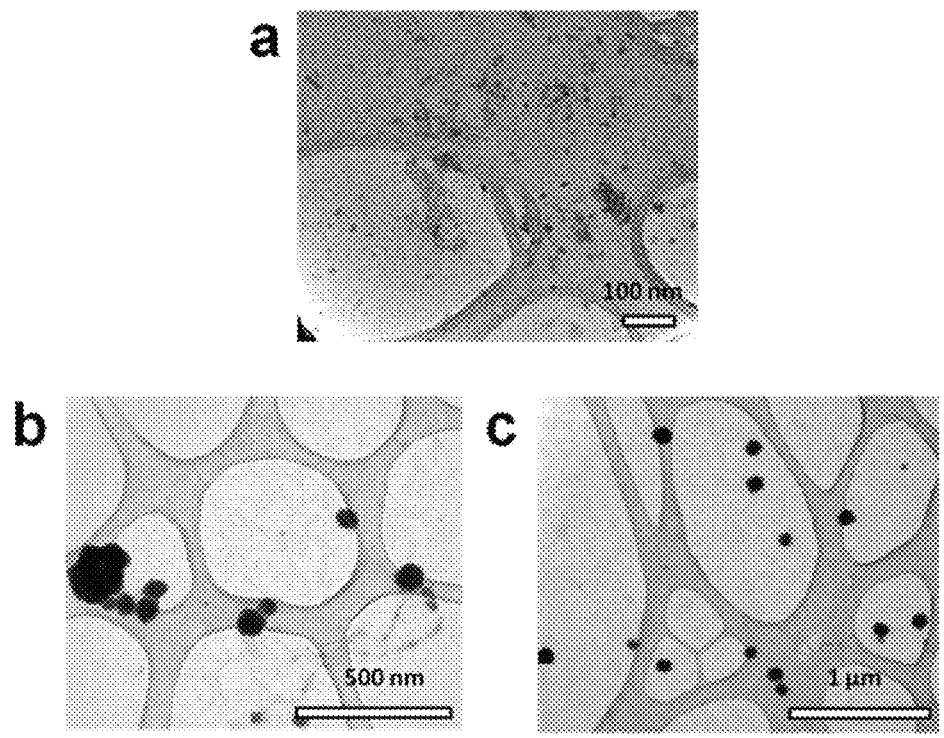

FIGS. 11A-11C. TEM study of morphological changes in 1:1 CdTe/CytC SPs in the course of the assembly. 3 hours (FIG. 11A), 24 hours (FIG. 11B), and 72 hours (FIG. 11C). Gradual growth of SPs in size is accompanied by narrowing the size distribution. As such, the size distribution of SPs after 24 hours of assembly in FIG. 11B is visually wider than the particle size distribution after 72 hours of assembly in FIG. 11C. This is indicative of preferred SP diameter corresponding to an equilibrium state.

Figures 12A, 12B:
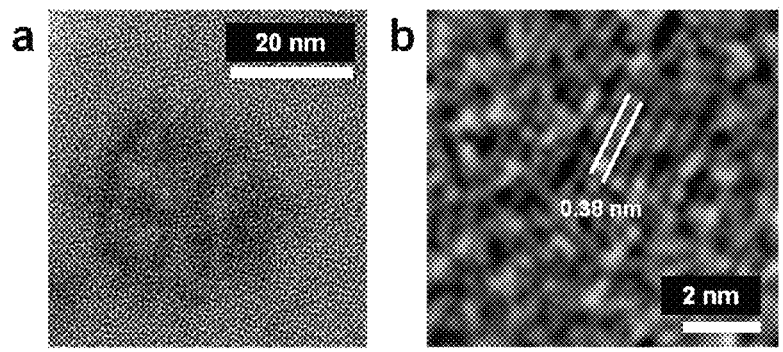

FIGS. 12A-12B. FIG. 12A shows an additional TEM image of individual CdTe/CytC SP. FIG. 12B shows an HRTEM image of an individual NP inside an SP in FIG. 12A demonstrating lattice spacing of 0.38 nm that corresponds to (111) zinc blend CdTe.

Figures 13A, 13B, 13C, 13D:
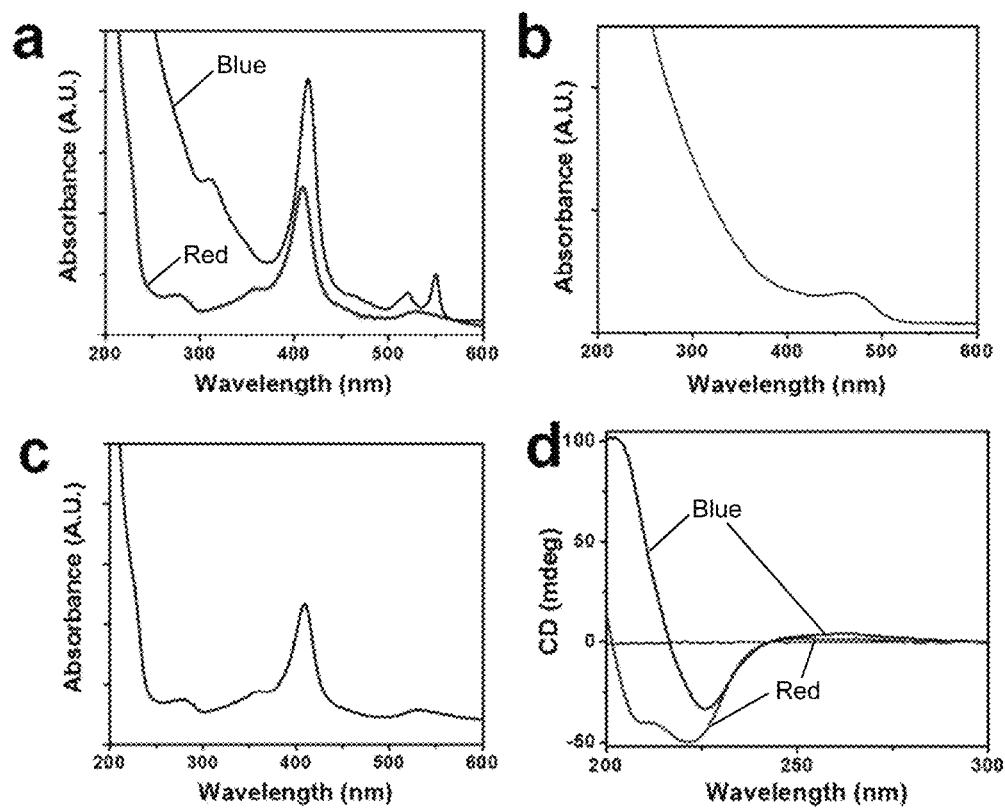
Figures 14A, 14B, 14C, 14D:
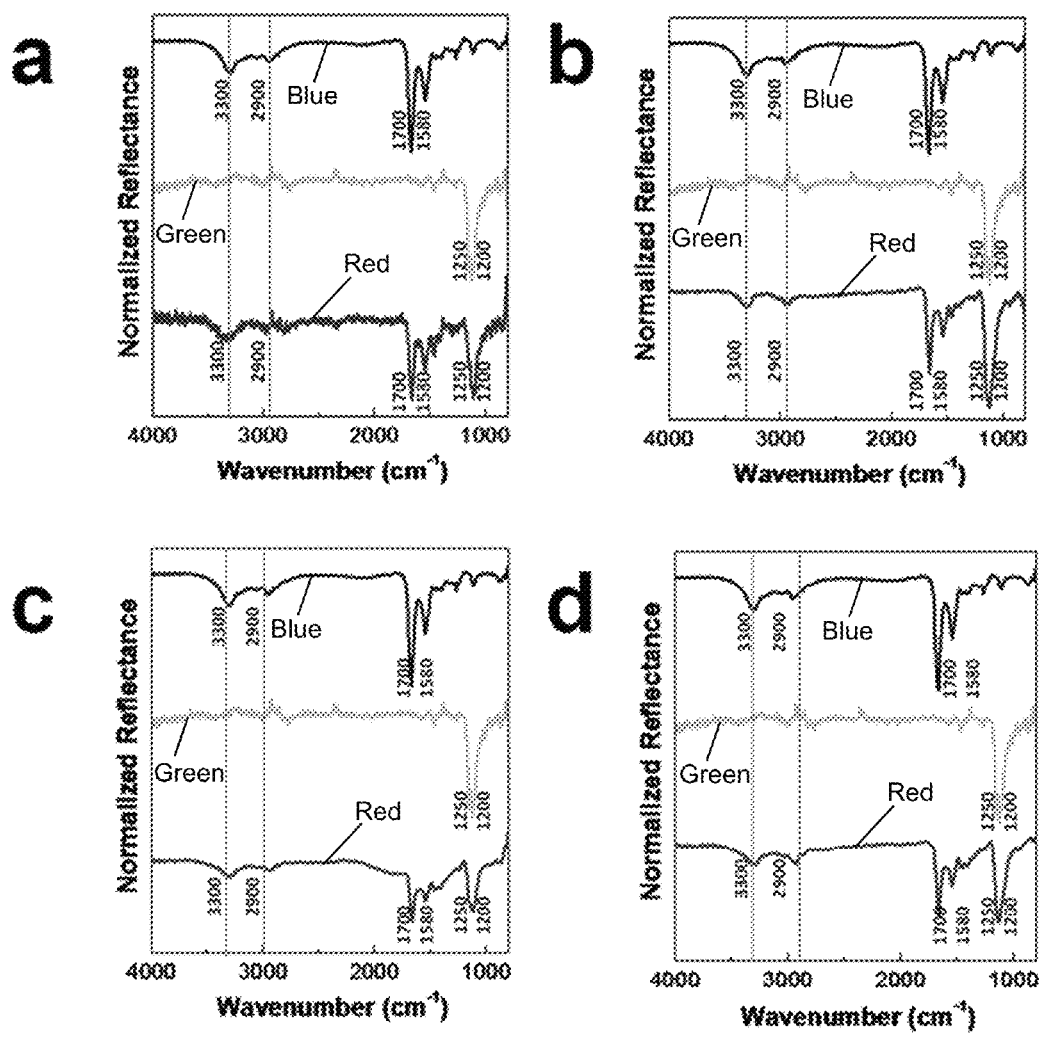

FIGS. 13A-13D. Characterization of CytC and its assemblies with CdTe NPs. FIG. 13A shows UV-Vis spectra of CytC (red, 5 μM) and SPs (blue, 1:1 CdTe/CytC, 72 hours). FIG. 13B shows UV-Vis spectrum of freely dispersed CdTe NPs. FIG. 13C shows a control experiment: UV-Vis spectrum of a mixture of $Cd(ClO_4)_2$ and CytC under the same conditions as in FIG. 13A. The spectrum of CytC in presence of $Cd^{2+}$ is identical to that without it. FIG. 13D shows CD spectra for free CytC (red, 6 μM), CdTe NPs (black, 6 μM), SPs (blue, 1:1 CdTe/CytC, 72 hours).

FIGS. 14A-14D. FTIR spectra of CytC (blue), CdTe NPs (green), and CdTe/CytC (red) assembly. FTIR spectra obtained after 1 hour (FIG. 14A), 12 hours (FIG. 14B), 24 hours (FIG. 14C), and 72 hours (FIG. 14D) of assembly. No shifts in the peaks have been observed. Peaks assignment: 3300 $cm^{-1}$ (N—H bond), 2900 $cm^{-1}$ (O—H bond), 1700 and 1580 $cm^{-1}$ (C=O bond), 1250 $cm^{-1}$ (C—N bond), 1200 $cm^{-1}$ ($CH_3$).

Figures 15A, 15B:
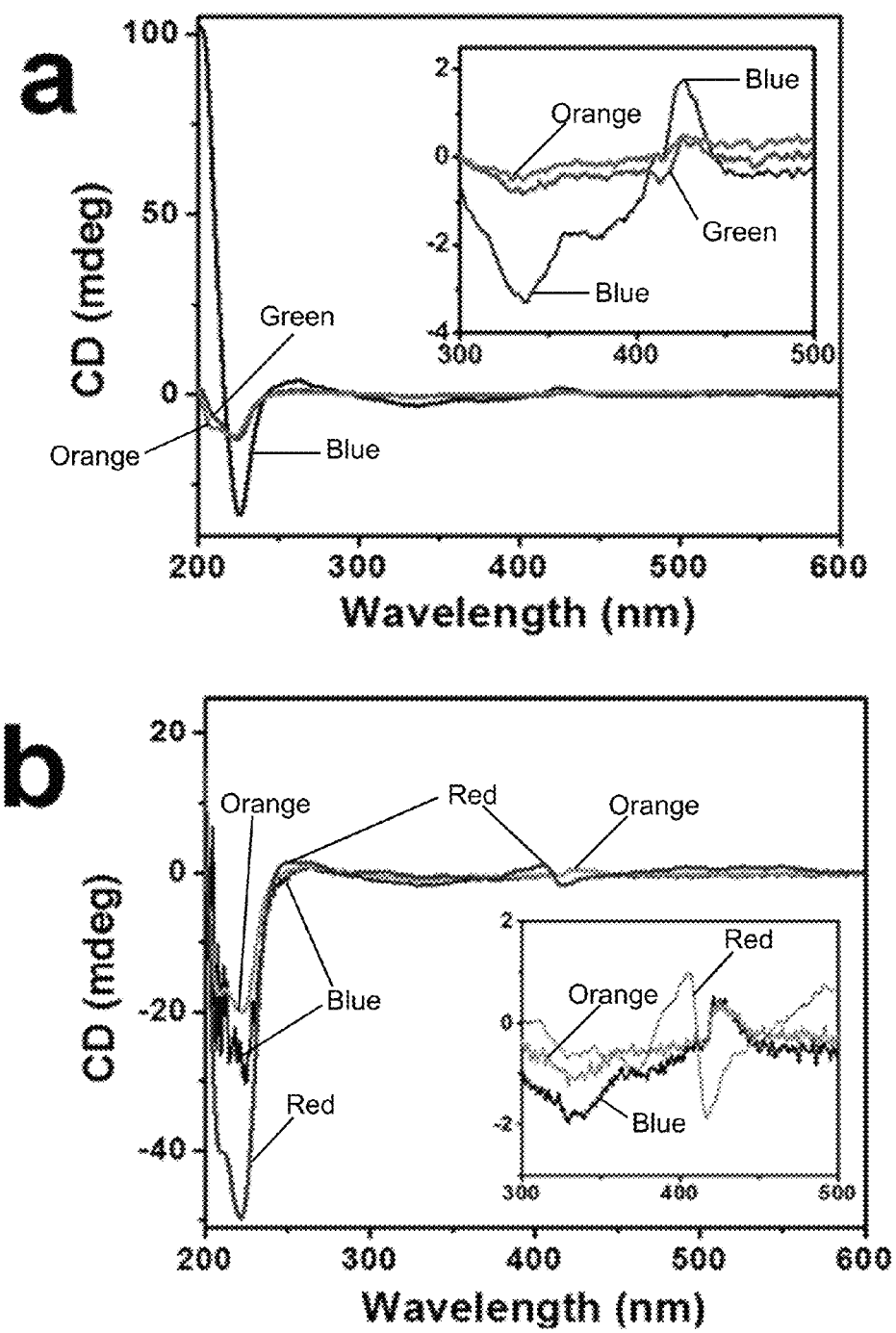

FIGS. 15A-15B. Control experiments for attribution of peaks in CD spectra. FIG. 15A shows CD spectra for different concentrations of SPs: 6 (blue), 3 (green), and 1.5 (orange) μM based on CdTe NPs. No change in the peak positions is observed; only the intensity of the peaks changed. This observation indicated that, indeed, the CD peaks being discussed are associated with SPs and not some other agglomerated states of CytC or NPs. FIG. 15B shows CD spectra for different components of SP dispersion: redispersed SPs separated from the original supernatant by centrifugation (blue), supernatant with SP removed (orange), and original CytC (red, 6 μM).

Figures 16A, 16B:
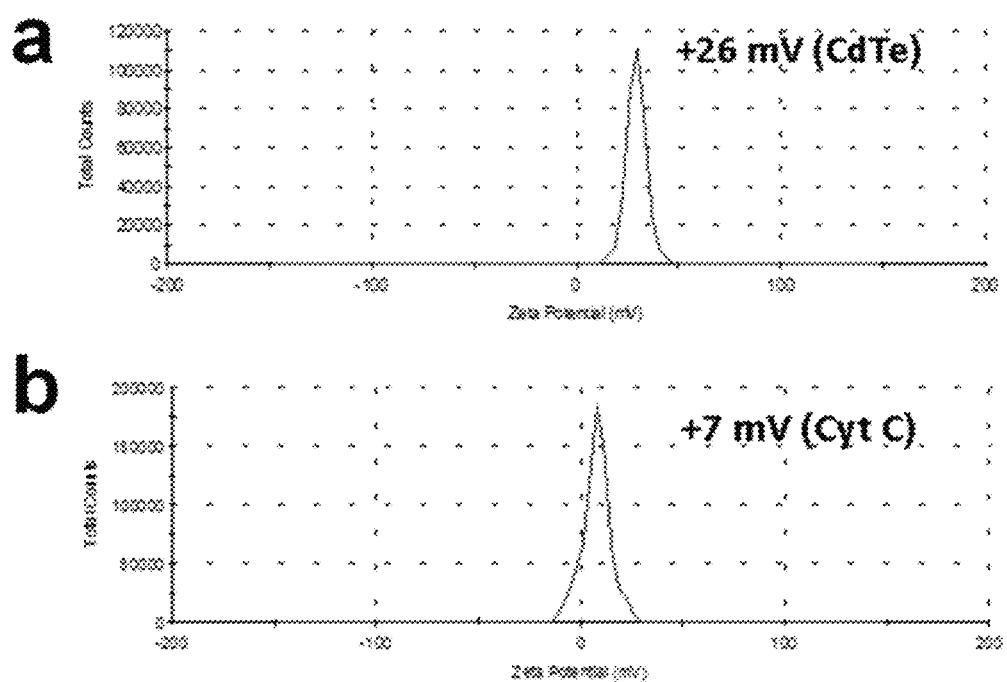

FIGS. 16A-16B. Electrokinetic ξ-potential measurements of DMAET-CdTe NPs (FIG. 16A); CytC at pH of about 5 (FIG. 16B).

Figures 17A, 17B, 17C:
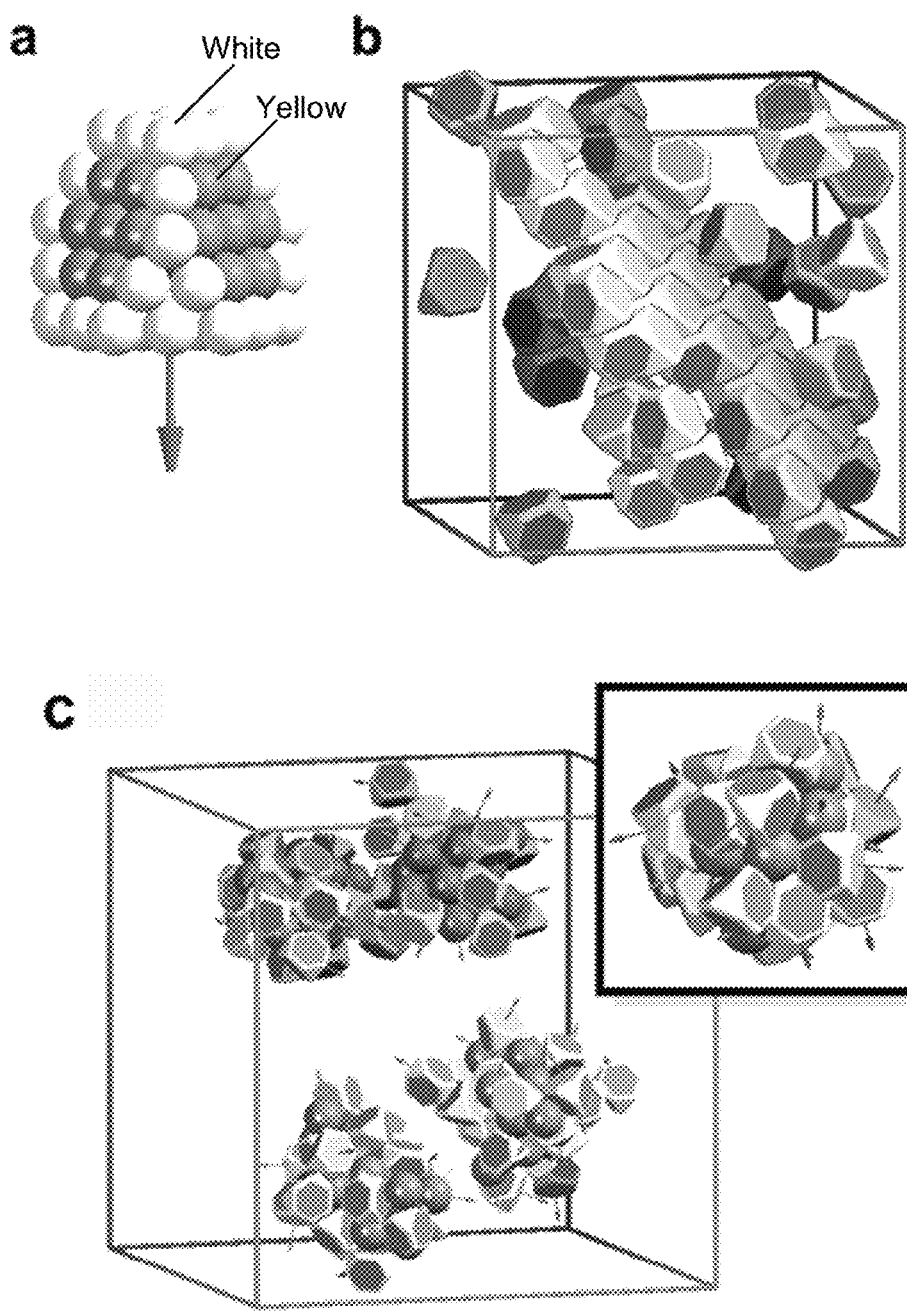

FIGS. 17A-17C. First-level coarse-graining model. FIG. 17A shows truncated tetrahedral NPs with the dipole vector (arrow) and attractive faces (yellow). FIG. 17B shows two-dimensional sheet formed by NPs. FIG. 17C shows spherical assemblies formed by a 1:1 mixture of 64 NPs and 64 CytC units. The NP faces and edges are drawn as smooth to better show the packing of the NPs within the sheet. Unlike in chains and sheets, the dipole moments of NPs and CytC within the spherical SPs do not exhibit any long-range correlation, indicated by a random orientation of their dipole moments (FIG. 17C, inset), presumably due to the strong screening effects and the flexible conformation of CytC.

Figures 18A, 18B, 18C, 18D:
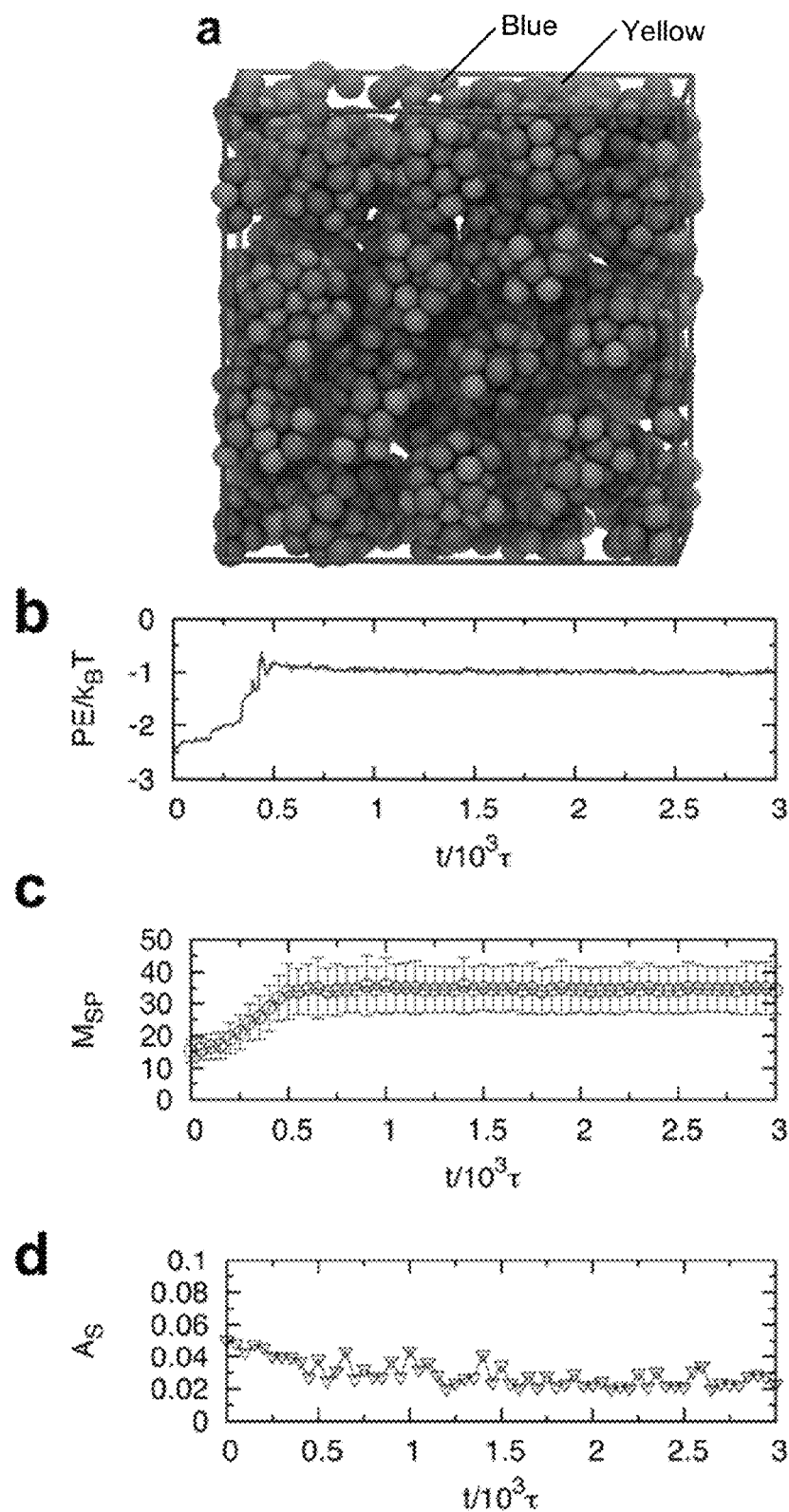

FIGS. 18A-18D. Time profile of the simulated self-assembly of SPs. FIG. 18A shows a snapshot of a 1:1 mixture consisting of N=2000 NP and CytC units after 2000 $\tau$ equilibration at number density of $\rho=N/V=0.125\sigma^{-3}$. FIG. 18B shows a system potential energy per unit upon compression from $0.001\sigma^{-3}$ to $0.125\sigma^{-3}$ followed by equilibration at $0.125\sigma^3$. FIG. 18C shows dependence of the number of structural units per SP, ($M_{SP}$), and FIG. 18D shows average asphericity parameter ($A_S$) of the SPs on the time of the assembly. Error bars in FIG. 18C are obtained from averaging over the SPs assembled in the system at the given time. The asphericity parameter $A_S$ characterizes the shape of the SP: $A_S=0$ corresponds to a perfectly spherical shape, $A_S=1$ corresponds to an infinitely long cylinder.

Figures 19A, 19B, 19C, 19D, 19E:
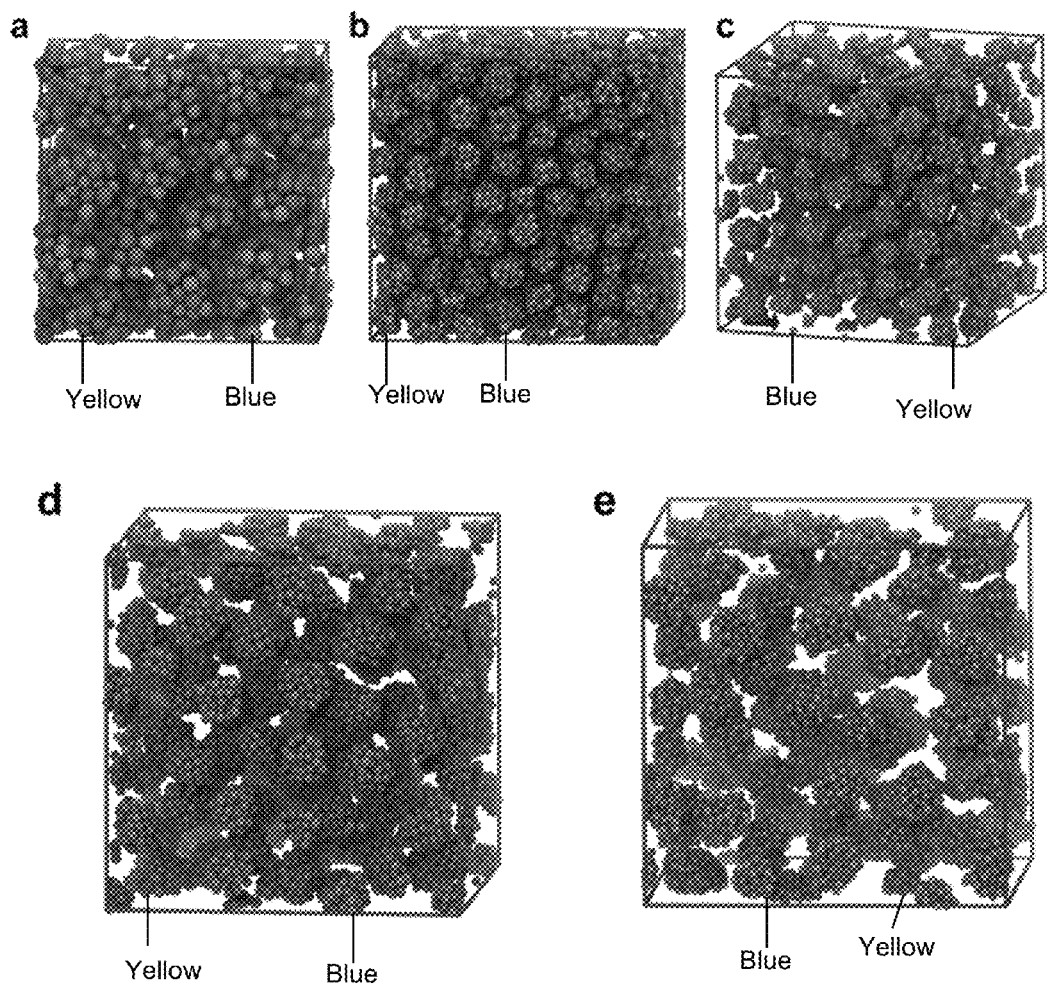

FIGS. 19A-19E. Simulation results of assembly of highly concentrated CdTe NPs and CytC. FIG. 19A shows a snapshot of a 1:1 mixture of NPs and CytC consisting of N=2000 units (NPs and CytC) in total in a cubic box with the size of L=20$\sigma$. The SPs are ordered into a face-centered cubic lattice. Each SP consists of $M_{SP}$=35 building blocks on average. FIG. 19B: N=16000, L=40$\sigma$, $M_{SP}$=35; FIG. 19C: N=16000, L=50$\sigma$, $M_{SP}$=54; FIG. 19D: N=13000, L=45$\sigma$; $M_{SP}$=80; FIG. 19E: N=13000, L=50$\sigma$, $M_{SP}$=118. The images are generated using the software VMD.

Figures 20A, 20B, 20C:
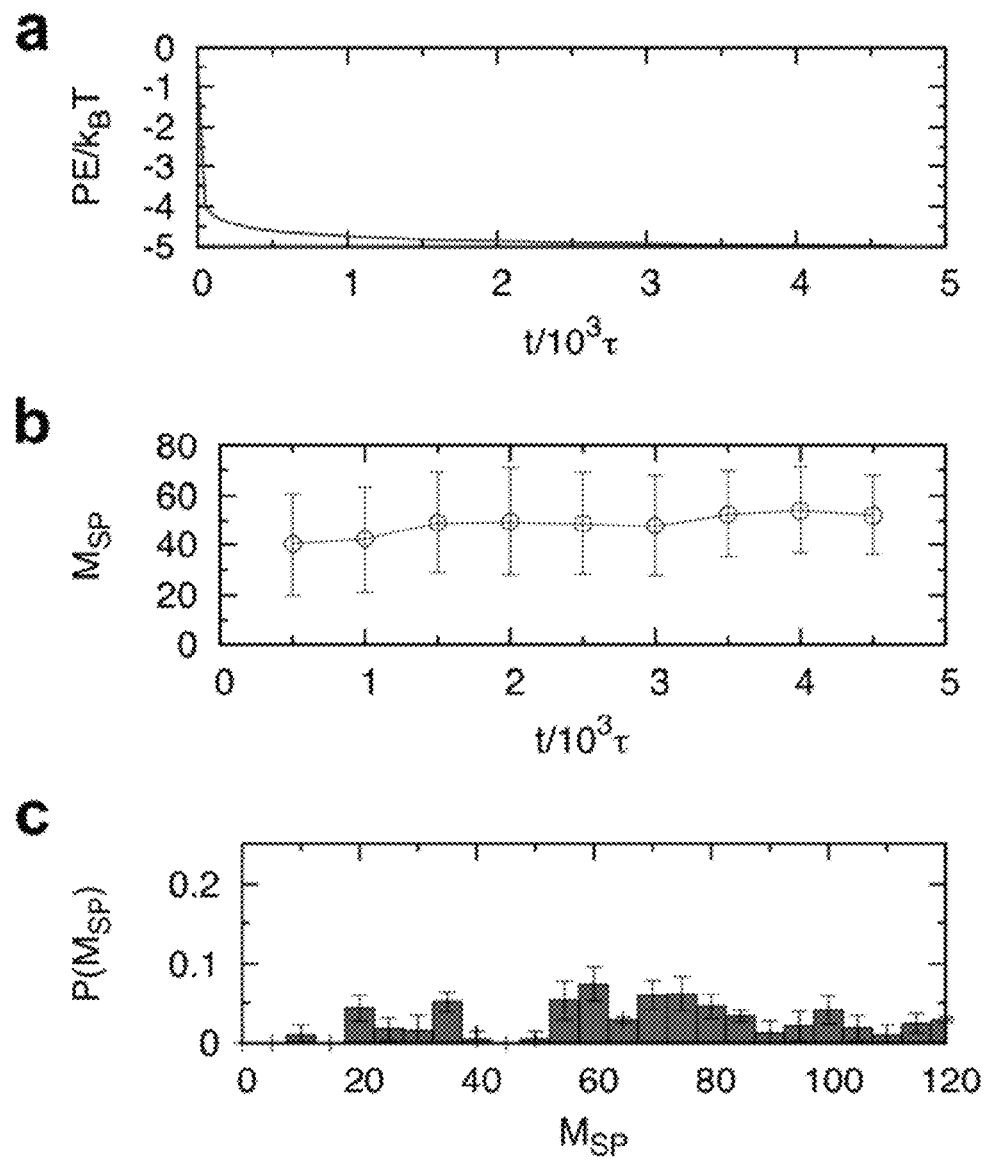

FIGS. 20A-20C. Simulation results without inter-SP charge-charge repulsion. FIG. 20A shows 1:1 mixture of NPs and CytC consisting of N=16000 units in total in a cubic box with the size of L=91$\sigma$ when the inter-SP repulsion is not renormalized. FIG. 20A is potential energy, FIG. 20B is average number of building blocks, and FIG. 20C is SP size distribution.

Figures 21A, 21B, 21C:
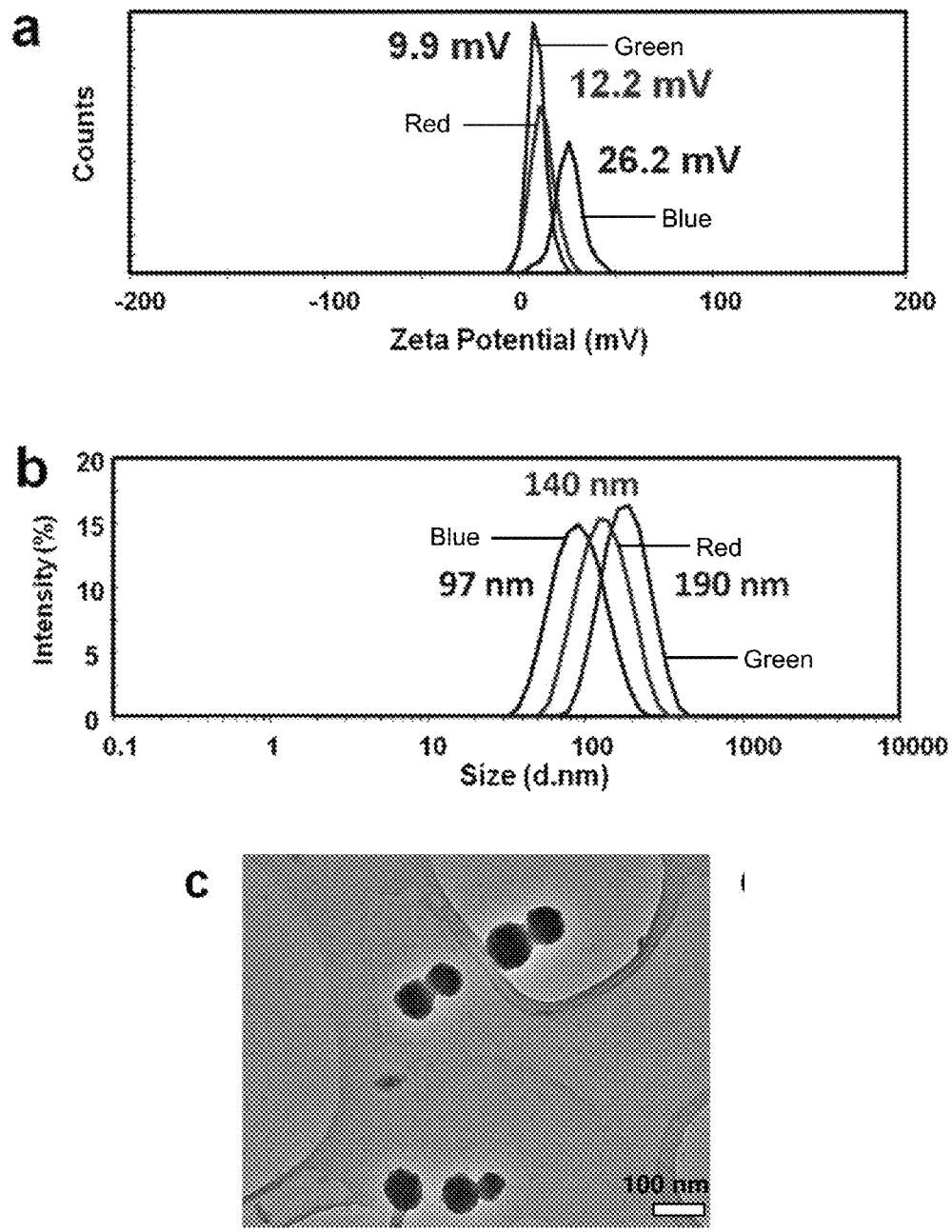
Figure 21D:
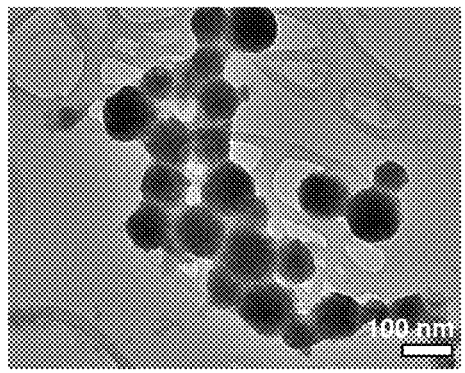
Figure 21E:
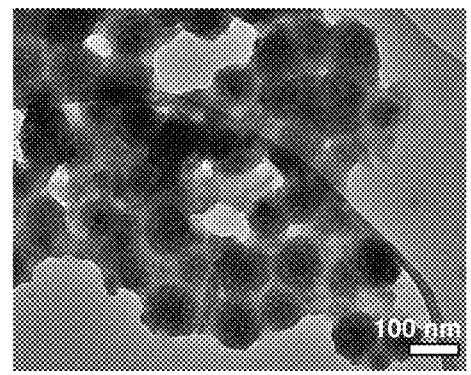
Figure 21F:
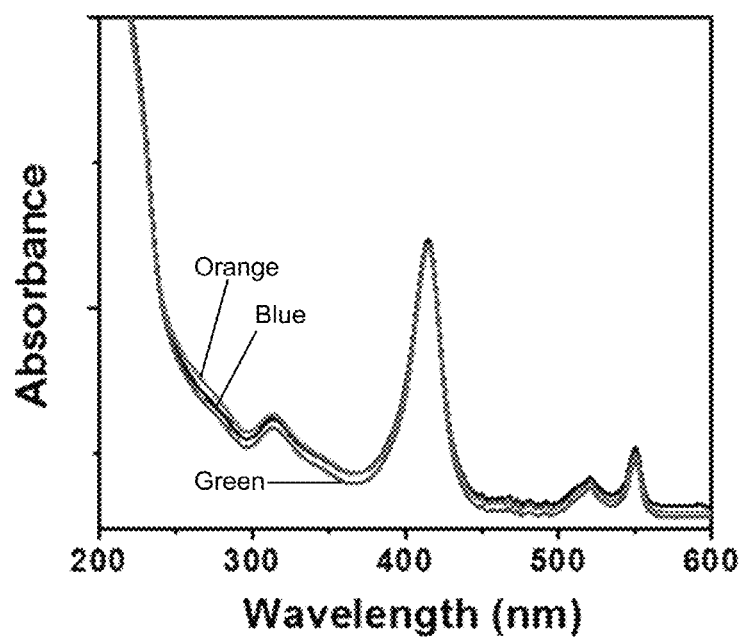
Figure 21G:
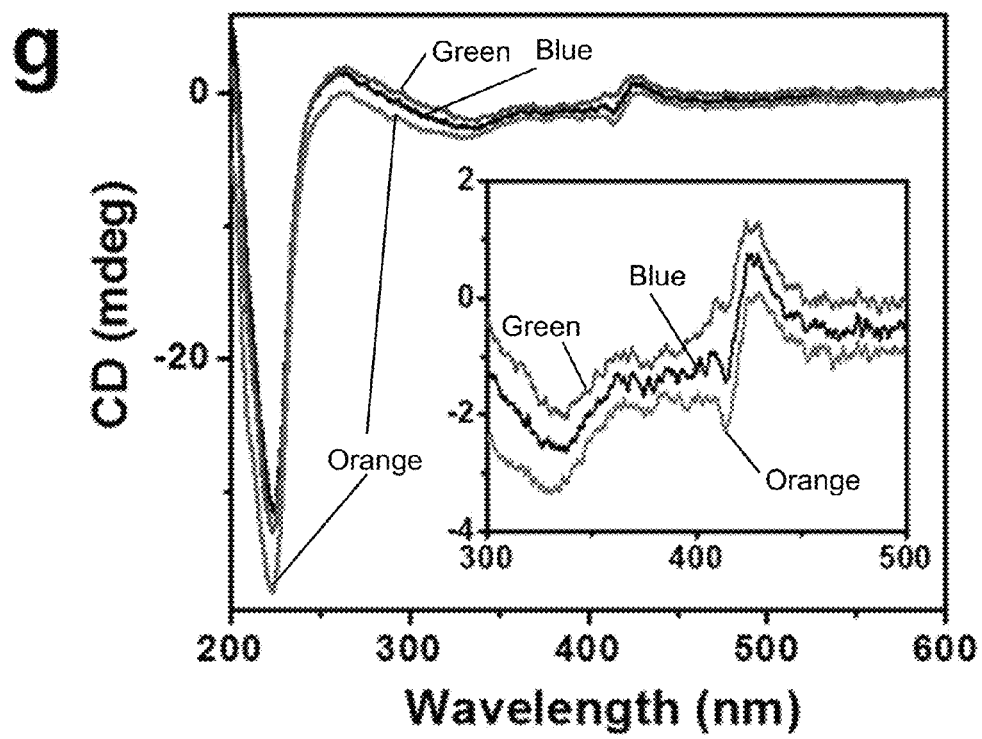
Figure 21H:
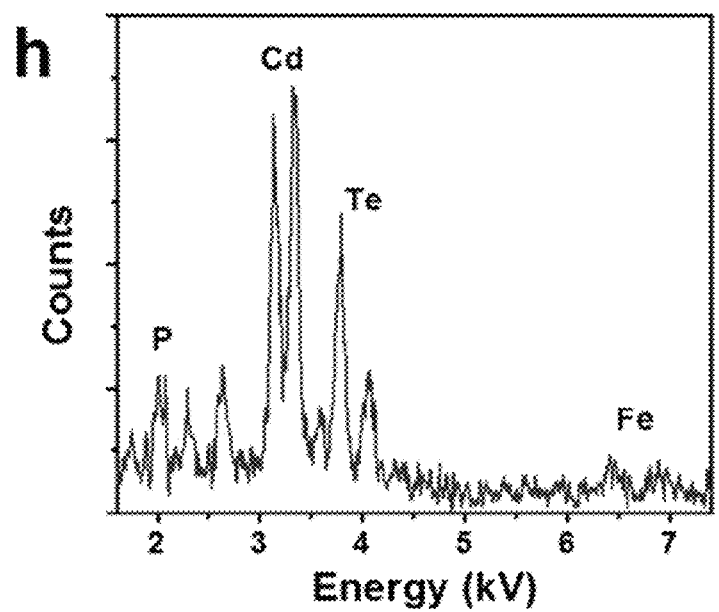

FIGS. 21A-21H. Co-assembly of 1:1 CdTe/CytC SPs and NRed into multicomponent SPs. FIGS. 21A-21B show electrokinetic $\xi$-potential and the DLS diameters of original NP-CytC SPs (blue) and SPs in presence of NADPH (red) and SP-NRed in presence of NADPH (green). FIGS. 21C-21E show TEM images of NP-CytC SPs, SPs in presence of NADPH, and SP-NRed in presence of NADPH. All scale bars are 100 nm. FIGS. 21F-21G show UV-Vis and CD spectra of SPs (blue), SPs in presence of NADPH (green), and SP-NRed in presence of NADPH (orange). FIG. 21H shows EDX spectrum of SPs in presence of NADPH in FIG. 21D showing the presence of phosphorous indicating SP-bound NADPH.

Figure 22:
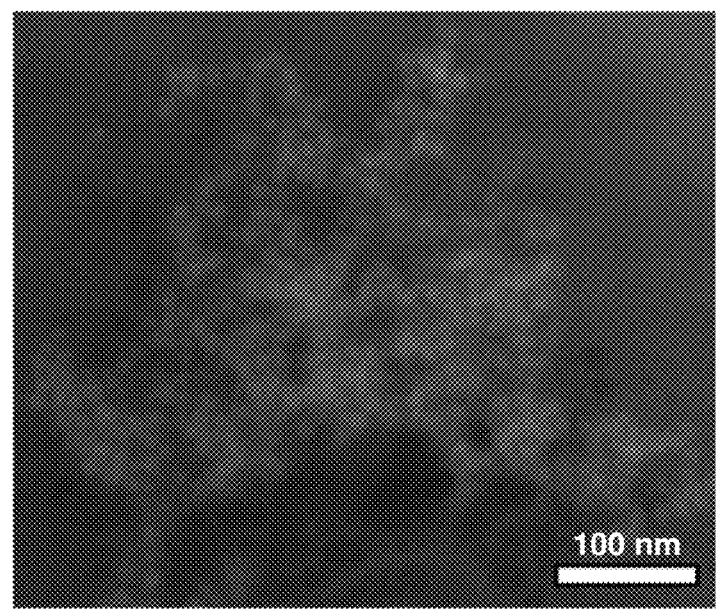

FIG. 22. Scanning electron microscopy image of SP-NRed in presence of NADPH. No change in spherical morphology compared to original 1:1 CdTe/CytC SPs is observed. Scale bar is 500 nm.

Figure 23:
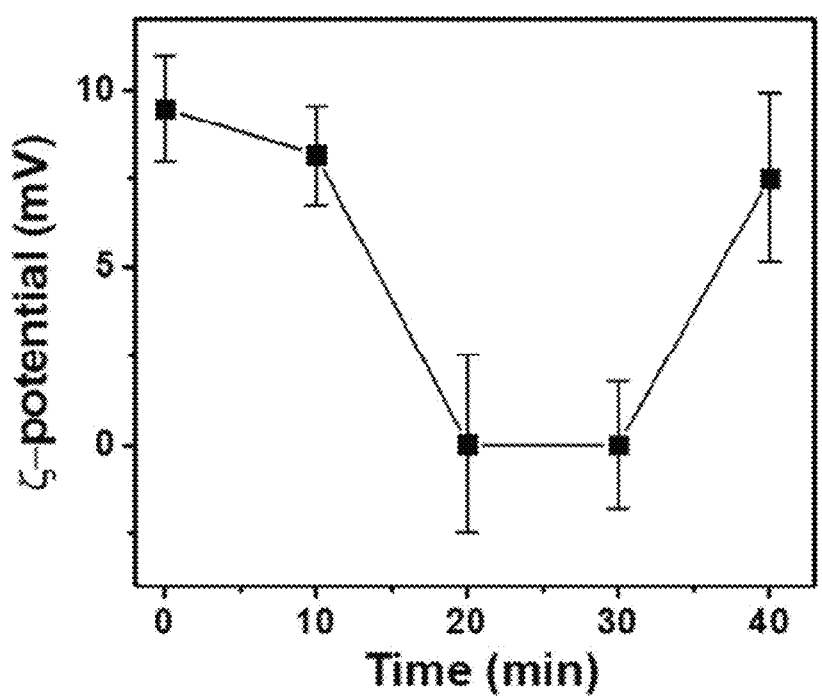

FIG. 23. A plot of electrokinetic $\xi$-potential of SP-NRed in presence of NADPH measured in the course of the photoenzymatic reaction.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

It should be understood for any recitation of a method, composition, device, or system that "comprises" certain steps, ingredients, or features, that in certain alternative variations, it is also contemplated that such a method, composition, device, or system may also "consist essentially of" the enumerated steps, ingredients, or features, so that any other steps, ingredients, or features that would materially alter the basic and novel characteristics of the invention are excluded therefrom.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters.

In addition, disclosure of ranges includes disclosure of all values and further divided ranges within the entire range, including endpoints and sub-ranges given for the ranges.

Various approaches for stabilizing proteins, especially enzymes, have been attempted, including protein engineering, chemical modification and immobilization. Enzyme immobilization is often used in industrial operations for operational stability and durability, as well as for the easy separation of products and the low costs of operation. However, these conventional immobilization methods only provide a moderate improvement in enzyme stability. Moreover, enzymes usually have enhanced stabilities after immobilization, but exhibit far lower activities as compared with free enzymes, mainly attributable to the loss of activity during the immobilization procedure and the mass-transfer limitations in solid supports. Thus, while there is a need to protect enzymes, for example, by encapsulation, there is also a need to retain access to the active centers within the enzyme for functionality. Stabilization of proteins and, in particular enzymes, while retaining high levels of catalytic activity, remains a significant technical challenge in various chemical and biochemical industries.

Stability of enzymes adsorbed onto nanoparticles is dependent on nanoparticle size and adsorption pattern. Protein and nanoparticle interactions during adsorption can cause conformational changes to an enzyme's native structure, rendering it inactive. Certain nanoparticles can form assemblies with biomolecules, such as proteins and enzymes, which are called supraparticles. Superstructures formed from cooperative assemblies are different from their individual components in terms of topology and dynamics. They are often found in nature as viruses or in membranes of biological molecules. Conventional processes for forming nanoassemblies having both nanoparticles and biomacromolecules have relied on attraction of opposite charges (between the nanoparticles having a first charge and the biomolecules having a second opposite charge). However, formation of such nanoassemblies with opposite charges, e.g., via ionic bonding, can be difficult to control and may either form core-shell morphologies or may form non-round supraparticles, such as nanoparticle plates interleaved between biomolecules that create "nanoflowers" or other similar structures. Such conventional core-shell or nanoflower structures may inhibit activity of the protein/enzyme bound therein.

In accordance with certain aspects of the present disclosure, a supraparticle is provided that comprises at least one nanoparticle species having a surface with a first charge and at least one protein species having a second charge. The second charge is the same as the first charge. Thus, in contrast to conventional supraparticle systems having oppositely charged protein and nanoparticles, in accordance with various aspects of the present disclosure, the nanoparticle(s) and the protein(s) are selected to have the same charge or polarity. The nanoparticle species and the protein species having the same charge self-assemble and associate with one another to form the terminal supraparticle nanoassembly. Notably, the supraparticle may comprise a plurality of nanoparticles of the same composition. Likewise, the supraparticle may comprise a plurality of proteins having the same composition. Thus, a plurality of nanoparticles and a plurality of proteins may be self-assembled to form a supraparticle. Further, in certain alternative aspects, one or more nanoparticle species having different compositions and/or one or more protein species having different compositions may be included in and form part of the supraparticle assembly. Importantly, the supraparticle assembly is created without any chemical bonding (e.g., intramolecular forces like covalent or ionic chemical bonding), but only via weak intermolecular forces (e.g., like dipole-dipole forces, Van der Waals forces, ion-dipole forces). Thus, the nanoparticle and the protein are associated with one another via intermolecular forces.

Nanoparticles are known to self-assemble into larger structures through growth processes that typically occur continuously and depend on the uniformity of the individual nanoparticles. Self-organization of semiconductor or metal nanoparticles (NPs) leads to nanoscale and microscale superstructures with geometries reminiscent of those produced by biological macromolecules. Terminal assemblies are those that are formed with inherent size restrictions in all directions. Here, inorganic nanoparticles can spontaneously form terminal assemblies in the presence of a protein or enzyme, forming uniformly sized substantially round terminal assemblies of supraparticles. This self-limiting growth process is believed to be governed by a balance between electrostatic repulsion and van der Waals attraction. The supraparticles can form from virtually any protein/enzyme with various nanoparticles. The generic nature of the interactions creates flexibility in the composition, size and shape of the constituent nanoparticles and proteins, and leads to a capability of forming a vast array of self-assembled nanostructures, including hierarchically organized colloids. In accordance with the present disclosure, such assemblies form spontaneously and represent a simple technological step for superior enzyme stabilization. The association of proteins and enzymes with nanoparticles provides a solution to various issues that arise in conventional immobilization systems, including providing minimum diffusional limitation, maximum surface area per unit mass, and high protein or enzyme loading. In this regard, the present technology is capable of increasing stability of various proteins or enzymes, while at the same time, maintaining high levels of activity for the proteins or enzymes. In this regard, the supraparticle assemblies provide extended shelf life for various products comprising proteins/enzymes and expand a range of conditions where the enzyme-based products can be used.

By selecting the appropriate nanoparticle species and protein species, the present disclosure provides relatively simple methods for making complex bio-nano systems. In certain aspects, the nanoparticle species has an average particle size diameter of greater than or equal to about 1 nm to less than or equal to about 100 nm; optionally greater than or equal to about 1 nm to less than or equal to about 50 nm; optionally greater than or equal to about 2 nm to less than or equal to about 40 nm; optionally greater than or equal to about 2 nm to less than or equal to about 30 nm; optionally greater than or equal to about 2 nm to less than or equal to about 20 nm; optionally greater than or equal to about 2 nm to less than or equal to about 15 nm; optionally greater than or equal to about 2 nm to less than or equal to about 10 nm; optionally greater than or equal to about 2 nm to less than or equal to about 8 nm; and in certain variations, optionally greater than or equal to about 2 nm to less than or equal to about 7 nm.

As noted above, the inventive technology in contemplated for use with a variety of different nanoparticles. In certain variations, the at least one nanoparticle may be selected from the group consisting of: gold (Au), silver (Ag), copper (Cu), nickel (Ni), iron (Fe), carbon (C), platinum (Pt), silicon (Si), cadmium (Cd), cadmium telluride (CdTe), cadmium selenide (CdSe), cadmium sulfide (CdS), mercury tellurium (HgTe), mercury selenide (HgSe), mercury sulfide (HgS), lead telluride (PbTe), lead selenide (PbSe), lead sulfide (PbS), molybdenum sulfide ($MoS_2$), iron (II) sulfide ($FeS_2$), iron sulfide (FeS), iron selenide (FeSe), zinc oxide (ZnO), and combinations thereof. Semiconductor nanoparticles, such as CdS, CdSe and CdTe (also known as quantum dots) can be useful for their ability to absorb energy and fluorescence. In certain variations, the nanoparticle may comprise a semiconductive/semiconductor material selected from the group consisting of: Cd, CdS, CdSe, CdTe, Si, ZnO and combinations thereof. In yet other variations, the nanoparticle comprises CdTe, $FeS_2$, or combinations thereof. In certain aspects, the nanoparticle comprises CdTe.

In certain aspects, the at least one nanoparticle may further comprise one or more stabilizers that enhances or evens out surface charge on a surface of the nanoparticle and further promotes stability of the supraparticle assembly. Thus, the stabilizer in certain preferred aspects has the same charge as the nanoparticle. Such stabilizers are well known and any variety of suitable stabilizers compatible with the selected nanoparticle is contemplated. In certain variations, a suitable stabilizer may be a thiol, a dithiol, a tertiary, secondary, or primary amino group, such as 2-(dimethylamino)ethanethiol (DMAET), ethanethiol amine, ethanolamine, monopropanolamine, and the like. In certain aspects, 2-(dimethylamino)ethanethiol (DMAET) is a particularly suitable stabilizer for use with the nanoparticle. In certain variations, the nanoparticle comprises CdTe and the stabilizer is 2-(dimethylamino)ethanethiol (DMAET), thus forming a DMAET-stabilized CdTe nanoparticle.

The protein is selected to have a second charge, which is the same as the first charge of the nanoparticle. A protein as used herein encompasses macromolecule chains comprising carbon, hydrogen, oxygen, nitrogen, and optionally sulfur, usually amino acids, where each amino acid residue is linked by covalent peptide bonds within the chain. A protein includes enzymes, peptides, polypeptides, hormones, antibodies, and the like. In certain aspects, the protein is an enzyme. The term "enzyme" generally refers to proteins that function as a biological catalyst to enable chemical transformations of organic compounds or catalyze biochemical or other reactions. Notably, certain enzymes are made of RNA fragments, which are also contemplated in certain alternative variations of the present teachings. A "denatured enzyme" refers to an enzyme that cannot function or has diminished functionality, because a shape has changed and its active site is altered, so that a target substrate cannot combine with the denatured enzyme's active site, resulting in loss of biological function and activity.

Enzymes may include those selected from the group consisting of: oxidoreductases, lyases, hydrolases, transferases, isomerases, ligases, and combinations thereof. In general, there are six classes or recognized types of enzymes (classified by the type of reaction that is catalyzed). Oxidoreductases are enzymes catalyzing reduction/oxidation or redox reactions are referred to generally as EC 1 (Enzyme Class 1). Transferases are enzymes catalyzing the transfer of specific radicals or groups are referred to generally as EC 2 (Enzyme Class 2). Enzymes catalyzing hydrolysis are referred to generally as EC 3 hydrolases. Lyases are enzymes catalyzing removal from or addition to a substrate of specific chemical groups are referred to generally as EC 4. Enzymes catalyzing isomerization are referred to generally as EC 5 isomerases. Ligases are enzymes catalyzing combining or binding together of substrate units, referred to generally as EC 6. Various enzymes are identified in ExplorEnz—the Enzyme Database at www.enzyme-database.org, the relevant portions of which are incorporated by reference.

Suitable proteins may be of a variety of types, such as the following non-limiting examples: hydrolase enzymes that catalyze hydrolysis of chemical bonds, including, but not limited to a lipase, a phosphatase, an amylase, a cellulase, a protease, a peptidase, a urease, or a deaminase. Specific examples of suitable hydrolases include but are not limited to, organophosphorus hydrolase (OPH), organophosphorus acid anhydrolase (OPAA), urease, butyrylcholinesterase or acetylcholinesterase. Transport proteins transport or store other chemical compounds and ions, including cytochrome C, an electron transport protein, hemoglobin and myoglobin oxygen transport proteins and albumin, a fatty acid transport protein in the blood stream. Hormones regulate various processes in organisms and are usually quite small and can be classified as peptides. Most known protein hormones are: insulin, growth factors, lipotropin and prolactin. Many protein hormones are precursors of peptide hormones, such as endorphin and enkephalin. Antibodies are proteins that are involved in the immune response, some of which can act as enzymes. Antibodies and protective proteins, such as lymphocyte antigen-recognizing receptors, antivirals agents, such as interferon and tumor necrosis factor, fibrin, thrombin (blood clotting proteins), and the like are contemplated. Structural proteins like collagen, elastin, keratin, sklerotin, fibroin, bacterial proteoglycans, and virus coating proteins are likewise contemplated. Motor proteins can convert chemical energy into mechanical energy, such as, actin and myosin. Receptors are proteins that are responsible for signal detection and translation into other types of signals, such as rhodopsin, a light detecting protein. Signaling proteins can also sometimes act as enzymes. Storage proteins contain energy, which can be released during metabolic processes, such as egg ovalbumin and milk casein.

Non-limiting examples of suitable enzymes for use in the supraparticle nanoassembly include proteases, amylases, lipases, cellulases, laccases, metalloproteinases, such as cytochromes, like cytochrome C oxidase, cytochrome P-450, superoxide dismutase, oxidases, like nitrate oxidase, dopamine β-hydroxylase, carboxylases, like ribulose-1,5-bisphosphate carboxylase/oxygenase, pyruvate carboxylase, carbonate dehydratase, biotin (as a carboxylase), ligases, urease, uricase, creatininase, esterases, pectinases, catalases, acylase, catalase, esterase, and any combinations thereof.

One or a plurality of enzymes or other proteins, or any combinations thereof, may be incorporated within the supraparticle assemblies of the present disclosure. Notably, in certain alternative variations, the present technology contemplates use of a variety of different biomolecules instead of or in addition to the at least one protein. For example, suitable biomolecules may include, by way of non-limiting example, co-enzymes, drugs or pharmaceutically active agents, antioxidants, free radical scavengers, nutrients, ligands, nucleic acids, DNA, RNA, polysaccharides, sugars, antibodies, immunomodulating agents, cytotoxin, targeting toxin agents, aptamers, and combinations thereof.

In certain aspects, a ratio of a nanoparticle (or nanoparticles) to protein (or proteins) in the supraparticle assembly is about 10:1 to about 1:10, optionally about 5:1 to about 1:5, optionally about 2:1 to about 1:2, and optionally about 1.5:1 to about 1:1.5. In certain embodiments, a ratio of the nanoparticle to the protein is about 1:1. While not limiting to any particular theory, it is believed that both the ratio of nanoparticle to protein species, as well as the particle size of the nanoparticle is important for promoting spontaneous self-assembly into substantially round uniformly sized terminal supraparticles without any intramolecular chemical bonding.

In aspects, a supraparticle nanoassembly formed from a nanoparticle species and a protein species (which may include a plurality of nanoparticles and protein molecules) is substantially round. "Substantially round-shaped" supraparticles have low aspect ratios and also having a morphology or shape including spherical, spheroidal, hemispherical, disk, globular, annular, toroidal, cylindrical, discoid, domical, egg-shaped, elliptical, orbed, oval, and the like. A low aspect ratio (AR) (defined as a length of the longest axis divided by diameter of the component) is typically less than or equal to about 10, and in certain preferred variations, equal to about 1. In certain preferred variations, the morphology of the supraparticle assembly has a spherical shape.

In certain aspects, a supraparticle comprising a nanoparticle species and a protein species has a longest dimension that is less than or equal to about 5 µm, optionally less than or equal to about 4 µm, optionally less than or equal to about 3 µm, optionally less than or equal to about 2 µm, optionally less than or equal to about 1.5 µm, optionally less than or equal to about 1.25 µm, and in certain preferred aspects, less than or equal to about 1 µm. In certain aspects, a supraparticle nanoassembly has at least one spatial dimension, such as an average supraparticle diameter, that is greater than or equal to about 50 nm and less than or equal to about 500 nm, optionally greater than or equal to about 50 nm and less than or equal to about 400 nm, optionally greater than or equal to about 50 nm and less than or equal to about 300 nm, optionally greater than or equal to about 50 nm and less than or equal to about 200 nm, optionally greater than or equal to about 60 nm and less than or equal to about 190 nm, optionally greater than or equal to about 70 nm and less than or equal to about 180 nm, optionally greater than or equal to about 80 nm and less than or equal to about 170 nm, and in certain variations, optionally greater than or equal to about 90 nm and less than or equal to about 160 nm.

Furthermore, in various aspects the supraparticles made in accordance with certain aspects have substantially uniform sizes, meaning that the supraparticles are monodisperse in size. Monodisperse generally refers to size distributions (e.g., particle diameter of each respective supraparticle assembly) that deviates less than or equal to about 25%, optionally less than or equal to about 20%, optionally less than or equal to about 15%, optionally less than or equal to about 10%, optionally less than or equal to about 5%, and in some aspects, less than or equal to about 1%.

A zeta potential ($\xi$) can be an important parameter for stability in colloidal system to facilitate self-assembly and formation of supraparticles. For example, in certain systems, a physically stable nanosuspension stabilized only by electrostatic repulsion ideally has a $\xi$-potential of ±25 mV at a minimum. In certain aspects, a stabilized supraparticle assembly comprising the nanoparticle and protein species has a zeta potential ($\xi$) of greater than or equal to about 25 mV, optionally greater than or equal to about 28 mV, optionally greater than or equal to about 29 mV, and in certain variations, optionally greater than or equal to about 30 mV. In certain aspects, a stabilized supraparticle assembly comprising the nanoparticle and protein species has a zeta potential ($\xi$) of greater than or equal to about 25 mV and less than or equal to about 50 mV, optionally greater than or equal to about 28 mV to less than or equal to about 40 mV, optionally greater than or equal to about 29 mV to less than or equal to about 40 mV, and in certain variations, optionally greater than or equal to about 30 mV to less than or equal to about 40 mV.

After formation of the supraparticle nanoassembly, in preferred aspects, the protein species retains greater than or equal to about 70% to about 100% of catalytic capability or catalytic activity as compared to the same protein species catalytic capability or activity in native or free form. In certain aspects, the protein in the supraparticle nanoassembly retains greater than or equal to about 90% of catalytic capability or activity, optionally greater than or equal to about 93%, optionally greater than or equal to about 95%, optionally greater than or equal to about 97%, optionally greater than or equal to about 98%, and in certain variations, optionally greater than or equal to about 99% of catalytic capability or activity as compared to the same protein's catalytic capability or activity in its native or free forms.

Thus, the present disclosure contemplates at least one nanoparticle species having a surface with a first charge and an average particle size diameter of greater than or equal to about 1 nm to less than or equal to about 100 nm and at least one protein species having a second charge that is the same as the first charge. The at least one nanoparticle and the at least one protein are associated with one another without chemical bonding and form a supraparticle nanoassembly having a substantially round shape. In certain preferred variations, the protein species is an enzyme.

Supraparticle assemblies in accordance with the present disclosure maintain the stability of proteins by keeping them in a folded state in the confines of the new hybrid supraparticle structure. The supraparticles can be used under many different conditions, including high temperatures. Thus, supraparticles provide protein and enzyme stabilization in a variety of harsh environmental conditions. Increased enzyme or protein stability within the supraparticle nanoassemblies can thus lead to formulation of better products, like improved detergents, fabric treatments, drugs, and the like. Such supraparticle assemblies also lend themselves to integration of optical and electric properties of metallic and semiconducting nanoparticles with the biological function of enzymes.

In certain aspects, the supraparticle nanoassemblies of the present disclosure can be dispersed in or associated with a medium (liquid, semi-liquid or gel, solid, or gas). For example, the supraparticle nanoassemblies can be distributed in a polymeric material and thus form composite materials. Likewise, supraparticle nanoassemblies can be dispersed in liquid or gel suspensions. Products including the supraparticles may be provided in liquid concentrates or as granules that can be added to other compositions. The supraparticle nanoassemblies according to the present disclosure can be used to stabilize proteins and retain activity and thus are useful in a wide variety of applications, including detergents, like laundry detergents, fuels, pulp and paper, fabric, textile, or leather treatments, pharmaceuticals, including drug formulations and drug delivery, implants, aerosols, sprays, wastewater treatment, solar fuel production, phototherapies, fuel production, including bioethanol and biofuel production, and the like.

In certain embodiments, a supraparticle assembly comprises a protein comprising cytochrome C protein (CytC) and a nanoparticle comprising cadmium telluride (CdTe). In certain aspects, the supraparticles in accordance with the present disclosure can be used to perform photoenzymatic reactions. Thus, nanoparticles in the supraparticle assembly can be selected for the ability to absorb irradiation or other energy to enhance the reactivity of the protein in the supraparticle. As noted above, the nanoparticle may be a semiconductor or other composition that is reactive to or capable of absorbing certain wavelength of light or other energy. Where the nanoparticle is capable of absorbing select wavelengths of light or energy, the light or energy can be directed at the supraparticle assembly to enhance the production of reaction products by greater than or equal to about 100% as compared to production when there is no irradiation directed at the supraparticle to result in enhanced photoreactivity, optionally greater than or equal to about 200%, optionally greater than or equal to about 300%, and in certain aspects, optionally greater than or equal to about 400% enhanced photoreactivity. Such supraparticle assemblies can be used for a variety of applications, including for solar fuel production. Similarly, such photoreactive supraparticles could be used as phototherapy agents. In other aspects, the nanoparticles may be magnetic, so that the SPs can be used for targeted drug delivery.

By way of non-limiting example, where supraparticles comprise cadmium telluride nanoparticles and Cytochrome C protein, as well as a redox enzyme and a sacrificial electron donor, the supraparticles are not only stable but demonstrate impressive photoenzymatic activity when irradiated with light. $NO^-_3$ reduction occurs by NRed, a nitrate oxidase, which is added to the SP, as well as a sacrificial electron donor (NADPH). When the supraparticle is irradiated with 470 nm light (absorption peak for CdTe), the production of $NO^-_2$ increased 4 times as compared to its production when there is no light irradiation.

A nanoassembly comprising CdTe nanoparticles having an average particle size diameter of about 3.8 nm with Cytochrome C (CytC) protein molecules having an average diameter of about 3 nm are formed and tested as described below. Spontaneous formation of spherical supraparticles (SP) containing both nanoparticles and protein components is observed with narrow size distribution. Self-limiting behavior is believed to be attributable to the dynamic process of SP growth leading to an equilibrium state, when electrostatic repulsive forces are balanced by multiple non-covalent attractive interactions. Experimental variation of SP diameters for several assembly conditions matches predictions obtained in simulations. Similar to micelles, supraparticles can incorporate other biological components as exemplified by incorporation of nitrate reductase. Tight packing of nanoscale components enables effective charge and exciton transport in supraparticles, as demonstrated by enzymatic nitrate reduction initiated by light absorption in the nanoparticle.

A supraparticle nanoassembly (SP) or protein-nanoparticle hybrid structure, which spontaneously assembles under variety of conditions, is formed from CdTe nanoparticles and Cytochrome C (CytC) enzyme. As noted above, SPs represent a case of stable self-limited terminal assemblies made possible by the equilibrium of attractive and repulsive forces between the NPs that make them similar to other terminal assemblies, for example, micelles and vesicles. Use of such SPs may include applications such as photoenzymatic activity, enhanced stability, and/or self-repair.

Positively charged CdTe NPs having a diameter of 3.8±0.4 nm, stabilized by 2-(dimethylamino)ethanethiol (DMAET), have been known to self-assemble into microscale sheets. For the "complementary" biomolecule, a well-studied protein, CytC having an average size of 3.1 nm and a dipole moment as high as about 340 Debyes (D). CytC does not reveal a tendency to self-assemble in solution without further manipulation. Its isoelectric point is pH 11.0, therefore it is positively charged over a wide pH range. Selection of a positively-charged protein for combining with positively charged nanoparticle seems to be counterintuitive to promoting self-assembly. Conventionally, electrostatic attraction between oppositely charged building blocks has been used to drive self-assembly. However, as contemplated herein and demonstrated below, counterbalancing electrostatic repulsion with intermolecular attractive interactions including dipolar, hydrogen bonding, hydrophobic, and van der Waals (vdW) forces successfully creates supraparticle assemblies from NPs and proteins, leading to terminal structures.

EXAMPLE 1

2-(dimethylamino)ethanethiol (DMAET)-stabilized CdTe nanoparticles (NPs) are synthesized as follows. Briefly, about 0.7 g of $Cd(ClO_4)_2 \cdot 6H_2O$ (Alfa Aesar) dissolved in 200 mL of water is mixed with about 0.45 g of DMAET (Sigma-Aldrich). Subsequently, pH of the medium is adjusted to be about 5.5 by addition of 0.1M HCl solution. The reaction mixture is placed in 250 mL-three neck round bottom flask with a septum, valve and condenser and is bubbled with $N_2$ gas for at least 30 min. $H_2Te$ gas formed by reacting about 0.2 g of $Al_2Te_3$ (Materion) with $0.5M\text{-}H_2SO_4$ is passed through the reaction mixture for 10 min at room temperature. Then, the reaction proceeded for 1-1.5 hours under magnetic stirring at 100° C. The reaction is stopped by cooling down the reactor at room temperature for about 30 min. The average diameter of the synthesized nanoparticles (NPs) is 3.8±0.4 nm.

Typically, 1 mL of NP dispersion containing 5-6 µM of NPs is precipitated at 4° C. for 24 hrs. Subsequently, the dispersion is centrifuged at 6000 rpm for 20 min at 15° C. The supernatant is discarded and the NPs are re-dispersed in 1 mL of water at pH 5 (adjusted by the addition of 0.1M HCl). Finally, the NP dispersion is mixed with 20 µl of 300 µM-CytC aqueous solution and is stored for 72 hrs.

Assembly of CdTe/CytC supraparticles (SPs). A 6 µM NP dispersion at pH 5 is mixed with 6 µM CytC at pH 7. The key biological function of CytC is to facilitate the electron transfer process in photosynthesis via redox reaction of the heme group ($Fe^{+2}/Fe^{+3}$) present in the core of the organic protein. The CytC (20 µL; 300 µM), CdTe NPs (dispersion—1 mL) and NRed (10 µl) are left at temperature 4° C., 20° C., 35° C., 55° C. and 70° C. during three days.

A stable NP-CytC dispersion with an electrokinetic potential ($\xi$) of +30 mV and pH about 5.3 formed after about 48-72 hrs. The presence of CytC strongly affects the NP assembly pattern. Examination by scanning electron microscopy (SEM) and transmission electron microscopy (TEM) reveals the formation of uniformly-sized, spherical SPs with a TEM diameter of $d_{TEM}$=94±5.6 nm (FIGS. 1A, 1E, 7A-7C) instead of large sheets typical of DMAET-CdTe NPs. The SPs size distribution is narrow with a standard deviation less than 7%. Dynamic light scattering (DLS) of 1:1 NP-CytC dispersion confirmed the assembly of SPs with $d_{DLS}$=99±19.0 nm (FIG. 1F), which matches the diameter determined from SEM/TEM data. The difference between $d_{DLS}$ and $d_{TEM}$ indicates incorporation of water molecules in the SPs, as is observed in many proteins and their assemblies.

Self-assembly into spheres is specific to the pairing of NPs and proteins in a 1:1 starting ratio. When NPs are the dominant component, there is an increasing tendency to form 2D structures (FIGS. 1B, 1C). When proteins are dominant, SP size distribution is increased and larger aggregates appeared (FIGS. 1D, 8). Within them, 100 nm SPs are identifiable, indicating a specific tendency of CytC+DMAET CdTe pairs to form spheres, unlike other geometries observed before.

The diameter of SPs shows limited dependence on the diameter of constitutive NPs. As such, the change in NPs size (average particle size diameter) from 2.7 nm to 7.2 nm results in a subtle change in diameter of SPs remaining largely within experimental error (Table 1). However, when the diameter of NPs increases to 13.5 nm, this is accompanied by a concomitant reduction in $\xi$, so that the average diameter of SPs increases dramatically to 970 nm (FIGS. 9A-9B). FIGS. 9A-9B shows SEM and TEM images of SPs assembled from 13.5 nm CdTe NPs and CytC under the same conditions as those in FIGS. 1A-1F and 2A-2F. The difference in size is shown, however, the uniformity and the shape of the SPs remains unchanged. Most of the further tests use 3.8 nm diameter NPs as the most representative and monodisperse to form assembled SPs.

TABLE 1

Dependence of supraparticle nanoassembly diameter on nanoparticle diameter.

| Diameter of DMAET-CdTe NPs (nm) | Zeta potential ($\xi$) (mV) | Diameter of SPs determined by DLS $d_{DLS}$ (nm) | Diameter of SPs determined by TEM $d_{TEM}$ (nm) |
|---|---|---|---|
| 2.7 ± 1.2 | 28.9 | 98 ± 22.3 | 91 ± 7.1 |
| 3.8 ± 0.4 | +30.7 | 99 ± 19.0 | 94 ± 5.6 |
| 6.5 ± 2.4 | +32.6 | 109 ± 13.5 | 93 ± 5.3 |
| 6.7 ± 1.1 | +35.9 | 133 ± 24.2 | 95 ± 3.4 |
| 7.2 ± 2.9 | +38.4 | 147 ± 20.8 | 98 ± 2.7 |
| 13.5 ± 2.3 | +0.27 | 1500 ± 96 | 970 ± 61 |

The effect of ionic strength and temperature of assembly on the diameter of SPs formed is explored here. The size of SPs considerably decreases when the ionic strength of the assembly medium increases (FIGS. 3A-3D, Table 2). The rise of the temperature of the solution results in a slight increase of SP diameter (Table 3). These trends are indicative of the possibility to control assembly patterns between CdTe and CytC using media parameters and represent elements of phase diagrams for SP assemblies.

TABLE 2

Dependence of supraparticle nanoassembly diameter on ionic strength.

| Concentration of NaCl (M) | Diameter of SPs determined by DLS $d_{DLS}$ (nm) | Diameter of SPs determined by TEM $d_{TEM}$ (nm) |
|---|---|---|
| 0.1 | 99 ± 19.2 | 94 ± 5.6 |
| 0.5 | 78 ± 17.4 | 75 ± 3.2 |
| 1.0M | 61 ± 12.2 | 54 ± 9.7 |
| 2.0M | 49 ± 23.1 | 45 ± 2.2 |

TABLE 3

Dependence of supraparticle nanoassembly diameter on temperature.

| Temperature (° C.) | Diameter of SPs determined by DLS $d_{DLS}$ (nm) | Diameter of SPs determined by TEM $d_{TEM}$ (nm) |
|---|---|---|
| 4 | 99 ± 19.2 | 94 ± 5.6 |
| 20 | 105 ± 21.3 | 98 ± 4.3 |
| 35 | 108 ± 17.4 | 99 ± 7.0 |
| 55 | 111 ± 18.1 | 102 ± 3.2 |
| 70 | 128 ± 26.5 | 123 ± 8.1 |

The intermediate stages of the self-organization process indicate the path by which the SPs form. The appearance of particles with $d_{DLS}$=126±9.7, 66±15.0, 72±9.4, and 100.6±17.3 nm are observed at 1, 24, 48, and 72 hours, respectively (FIG. 10). This is accompanied by a gradual disappearance of signals with $d_{DLS}$=5±0.4 and 20±1.4 nm, attributed to original NPs and early NP-CytC clusters, respectively. The initial increase and then decrease of $d_{DLS}$ values show that large aggregates with a broad size distribution formed quickly, and later condensed and stabilized in size by 72 hours. The sequence of the intermediate stages preceding formation of stable SPs is confirmed by TEM images (FIGS. 11A-11B).

High resolution transmission electron microscopy (HR-TEM) of the assemblies indicate that they consist of reticulated electron-transparent and electron-dense areas (FIGS. 2A, and 12A-12B) with typical dimensions of about 5 nm to about 7 nm. Tomographic 3D reconstruction images of the spherical SPs show that these areas interpenetrate (see vii and viii in FIG. 2B) to form a network of tightly interconnected NP and CytC units. X-ray energy dispersive spectroscopy (XEDS) confirmed the presence of both NP and CytC (FIG. 2C). Individual NPs in semiconductor-rich areas could be distinguished by the crystal lattice with periodicity of 0.38 nm expected for CdTe (111) lattice planes (FIG. 12B). No specific order is observed within the network although the tight packing with volume density of NPs considerably higher than percolation threshold makes it bi-continuous. The interconnectivity of the NPs, essential for charge and exciton transfer within SPs, is likely to be non-random and governed by modified percolation theory affected by the self-assembly phenomena.

Based on the average volume of the SPs and atomic ratio of Cd and Fe, the total number of CytC and NPs in a SP can be estimated to be $3.6 \times 10^3 + 7.5 \times 10^2$. The structures of individual SPs can be described by a schematic in FIG. 2D. Whether the process of SP formation (FIGS. 10, 11A-11B) causes a significant degree of structural change in the softer component, i.e., CytC molecules when it assembles with the more rigid components, the NPs explored here.

Absorbance peaks in the visible part of the spectrum of CytC in both $Fe^{3+}$ and $Fe^{2+}$ forms are associated with electronic $\pi$-$\pi^*$ transitions of the Fe-porphyrin complex that is also known as the heme group. The spectrum of $Fe^{+3}$-CytC shows the two primary peaks at 409 and 520 nm (FIG. 13A, red). Previous studies showed that the transition of $Fe^{+3}$-CytC into $Fe^{+2}$-CytC causes the red-shift of the strongest Soret-band (X of about 410 nm) and the emergence of new $\beta$- and $\alpha$-bands with $\lambda$ about 500 and 550 nm, respectively. The latter two are often called Q-bands. The reduction of $Fe^{+3}$-CytC into $Fe^{+2}$-CytC occurs (FIG. 13A). There is most-likely co-existence of both $Fe^{+3}$ and $Fe^{+2}$ forms of CytC all the time. The reduction is associated primarily with the transfer of electrons from CdTe core to CytC. DMAET ligands on the NPs surface can also serve as reducing agents as well.

Thus, during SP assembly, the $\pi$-$\pi^*$ peak of CytC at 409 nm (Soret band) red-shifted to 415 nm, while the shoulder at 500 nm split into two distinct peaks at 520 nm and 550 nm (FIGS. 13A-13D). Upon assembly, the UV-vis edge of CdTe NPs located at 490 nm in freely dispersed particles undergo a blue shift to 470 nm due to a change of dielectric environment around the NPs (FIGS. 13A-13B) when transition from water to CytC surroundings. These transitions indicate a change in the oxidation state of the heme group in the protein from $Fe^{+3}$ to $Fe^{+2}$ upon SP assembly; from the extinction coefficient of the $Fe^{+2}/Fe^{+3}$ at 550 nm it is estimated that ca 77% of the iron atoms are present in their reduced state in the assembled SPs. $Cd^{+2}$ ions do not cause any structural or electronic changes in $Fe^{+3}$-CytC at the mixing of 1:1 molar ratio (FIG. 13C).

From the extinction coefficient and absorbance of $Fe^{+3}$- and $Fe^{+2}$-CytC at 550 nm, the extent of heme reduction can be estimated. Extinction coefficients ($\in$) of $Fe^{+3}$- and $Fe^{+2}$-CytC at 550 nm are 8.4 and 28.0 $mM^{-1}$ $cm^{-1}$, respectively. The absorbance at 550 nm of CytC ($A_{CytC}$ about 0.25) and a mixture of CdTe/CytC at 72 hours ($A_{CdTe/CytC}$ about 0.18) is compared. From Beer-Lambert's law $$A = \in bc, \quad (6)$$

where b is the light path-length and c is the concentration of the chromophore, we obtained $[Fe^{+3}\text{-CytC}]$ and $[Fe^{+2}\text{-CytC}]$ as about 8.3 and 6.4 $\mu$M, respectively. This indicates about 77% degree of reduction.

After assembly with NPs, the protein remained in a folded state. Spectroscopic signatures of denaturation/unfolding of CytC are used to determine whether the destruction of the tertiary structure of the CytC protein is observed. A drastic change of UV-vis spectra of the heme occurring if the tertiary structure is unfolded exhibits a blue shift of the Soret band and disappearance of the peaks in 500-600 nm region, which does not occur for CytC in SPs (FIG. 13A). If the protein had denatured, it would have manifested as a blue shift of the Soret band and disappearance of the peaks in 500-600 nm region, neither of which is observed in this system (FIG. 13A). This conclusion is confirmed by essentially identical IR spectra of CytC before and after assembly with NPs (FIGS. 14A-14D).

It is also instructive to evaluate the CD and UV data upon assembly of CytC with other proteins, such as GroEL and cytochrome C oxidase. One can see clear parallels in the change of CytC conformation for assembly with CdTe NPs and these proteins. The CD data further substantiate that CytC incorporated in SPs retains its folded, although slightly conformationally altered, state. Original CytC had negative (−) CD peaks at 208 nm and 220 nm, corresponding to $\beta$-sheets and $\alpha$-helices, respectively (FIG. 13D). In the SPs, the positive CD peak representing $\alpha$-helices at 225 nm dominated, and a new negative peak appeared at 340 nm (FIGS. 2E, 13D). The conformational changes of CytC upon interactions with NPs are also confirmed by examining the Soret band CD peaks that appear for free CytC at 408 nm (+) and 418 nm (−), typical for the heme group. The corresponding CD peaks in the assembled SPs become red-shifted and change signs, (FIG. 2E) which correlates well with the change of redox state of iron in the intact heme. The dilution data in FIGS. 15A-15B confirm that these structural changes are intrinsic to SPs and are not due to intermediates or other macromolecular complexes. Such conformational changes are similar to those taking place in concentrated solutions of globular proteins.

Note also that the observed changes in CD, UV spectra and the conformational transitions upon assembly of CytC with NPs are reminiscent of those in CytC complexes with GroEL or Cytochrome C oxidase. FIGS. 15A-15B show control experiments for attribution of peaks in CD spectra. FIG. 15A has CD spectra for different concentrations of SPs: 6 (blue), 3 (green), and 1.5 (orange) $\mu$M based on CdTe NPs. No change in the peak positions is observed, only the intensity of the peaks changed. This observation indicates that, indeed, the CD peaks are associated with SPs and not some other agglomerated states of CytC or NPs. FIG. 15B shows CD spectra for different components of SP dispersion: redispersed SPs separated from the original supernatant by centrifugation (blue), supernatant with SP removed (orange), and original CytC (red, 6 $\mu$M). The CD spectrum of CdTe NP did not have any CD bands in this spectral window (FIG. 2E, black). The identity of the CD peaks of separated and re-dispersed SPs with those discussed in FIG. 2E (72 hours, blue) confirm the attribution of the CD peaks to SPs and not to potential specific selection of chiral NPs from the solution by interaction with the protein.

Now, the mechanism of the formation of spherical monodisperse SPs is further explored. Because the components are similarly charged, their formation is believed to be due to a self-limiting process in which the electrostatic repulsion between the NPs and protein is overcome by weak attractive interactions. The overall attractive potential between the similarly charged CdTe NPs and CytC can be confirmed by calculations based on classical and extended Derjaguin, Landau, Verwey, and Overbeek (DLVO) theory (FIG. 3H).

Even within the limits of the classical DLVO the aggregation barrier in pair potential is smaller than $k_B T$. The extended DLVO interaction energies between quantum dots are approximated by the following expression:

$$V_{EDLVO} = V_{vdW} + V_{DL} + V_{DP} + V_{Q-DP} + V_{HB},$$

where $V_{vdW}$, $V_{DL}$, $V_{DP}$, $V_{Q-DP}$, $V_{HB}$ are van der Waals (vdW), double layer electrical repulsion (DL), dipole-dipole (DP), charge-dipole (Q-DP), and hydrophobic (HB) interaction potentials, respectively.

Van Der Waals Interaction Potential

Total van der Waals potential between CdTe NPs capped with a shell of DMAET and Cytochrome C (CytC) can be evaluated as follows:

$$V_{vdW} = V_{vdW,CdTe-CytC} + V_{vdW,DMAET-CytC},$$

where $$V_{vdW,CdTe-CytC} =$$

-continued $$\frac{-(\sqrt{A_{11}}-\sqrt{A_{44}})(\sqrt{A_{33}}-\sqrt{A_{44}})H_{CdTe-CytC}(m,n)}{12}: m=\frac{x+d}{2R_{CdTe}},$$

$$n=\frac{R_{CytC}}{R_{CdTe}}$$

$$V_{vdW,DMAET-CytC}=$$

$$\frac{-(\sqrt{A_{22}}-\sqrt{A_{44}})(\sqrt{A_{33}}-\sqrt{A_{44}})H_{DMAET-CytC}(m,n)}{12}: m=$$

$$\frac{x}{2(R_{CdTe}+d)},$$

$$n=\frac{R_{CytC}}{R_{CdTe}+d}.$$

H(m,n), the Hamaker function, is given by $$H(m,n)=\frac{n}{m^2+mn+n}+\frac{n}{m^2+mn+m+n}+2\ln\left[\frac{m^2+mn+m}{m^2+mn+m+n}\right].$$

Here, x is the closest distance between the DMAET-capped CdTe NPs and CytC. $A_{11}$ (11.4×10$^{-20}$ J), $A_{22}$ (7×10$^{-20}$ J), $A_{33}$ (9.63×10$^{-20}$ J), $A_{11}$ (3.72×10$^{-20}$ J) are Hamaker constants for CdTe, hydrocarbons, proteins and water respectively. $R_{CdTe}$ (1.9 nm) is the radius of CdTe NPs, d (0.74 nm) is the thickness of the DMAET shell around the NPs, $R_{CytC}$ (1.55 nm) is the radius of CytC approximated as a spherical entity.

Double Layer Electrical Repulsion

Double layer repulsive potential between DMAET-capped CdTe NPs and Cytochrome C can be evaluated following references:

$$V_{DL}=$$

$$4\pi\varepsilon_o\varepsilon_r(R_{CdTe}+d)R_{CytC}\Gamma_{CdTe\_DMAET}\Gamma_{CytC}\left(\frac{k_BT}{e}\right)^2\frac{\exp(-\kappa x)}{x+R_{CytC}+R_{CdTe}+d}$$

where $$\Gamma_{CdTe\_DMAET}=\frac{8*\tanh\left(\frac{e\psi_{CdTe\_DMAET}}{4k_BT}\right)}{1+\sqrt{1-\frac{2\kappa(R_{CdTe}+d)+1}{(\kappa(R_{CdTe}+d)+1)^2}\tanh^2\left(\frac{e\psi_{CdTe\_DMAET}}{4k_BT}\right)}}$$

$$\Gamma_{CytC}=\frac{8*\tanh\left(\frac{e\psi_{CytC}}{4k_BT}\right)}{1+\sqrt{1-\frac{2\kappa R_{CytC}+1}{(\kappa R_{CytC}+1)^2}\tanh^2\left(\frac{e\psi_{CytC}}{4k_BT}\right)}}$$

where $\varepsilon_0$ is the permittivity of vacuum, $\varepsilon_r$ is the dielectric constant of water, $\psi_{CdTe-DMAET}$ is the zeta potential of DMAET-capped CdTe NPs (+26 mV), $\psi_{CytC}$ is the zeta potential of CytC (+7 mV). κ is the reciprocal double layer thickness (Debye length), is given by $$\kappa=\sqrt{\frac{1000N_Ae^2}{\varepsilon_r\varepsilon_0k_BT}\sum_i M_i\times Z_i^2}$$

where e is electric charge (Coulombs), $N_A$ is Avogadro's number, $M_i$ and $Z_i$ are the molar concentration and valency of ions, respectively. The Debye length of NaCl electrolytes specific to ionic strength of interest is calculated accordingly. The practical Debye length of water is taken to be $\kappa^{-1}\approx 100$ nm.

Dipole-Dipole Interaction Energy

Dipole-dipole energies is derived according to the interaction model and is approximated by the following:

$$V_{DP}=$$

$$\frac{-\mu_{CdTe}\mu_{CytC}}{2\pi\varepsilon_o\varepsilon_r}*\frac{(x+R_{CdTe}+R_{CytC}+d)}{x(x+2R_{CdTe}+2d)(x+2R_{CytC})(x+2R_{CdTe}+2R_{CytC}+2d)}$$

where $\mu_{CdTe}$ (100D) and $\mu_{CytC}$ (340D) are dipole moment of CdTe NPs and CytC, respectively.

Charge-Dipole Interaction Energy

Charge-dipole energy according to an interaction model is evaluated from the following:

$$V_{Q-DP}=$$

$$-\frac{\mu_{CytC}Q_{CdTe\_DMAET}-\mu_{CdTe\_DMAET}Q_{CytC}}{4\pi\varepsilon_o\varepsilon_r}*\frac{1}{(x+R_{CdTe}+2R_{CytC}+d)^2}$$

where $Q_{CdTe-DMAET}$ and $Q_{CytC}$ are the total surface charge of DMAET-capped CdTe and CytC respectively. Previously reported surface charge of CdTe NPs (+3e) is used. The surface charge of CytC is obtained from the following relations: $\sigma_{CytC}$ $$\sigma_{CytC}=\frac{2\varepsilon_r\varepsilon_o\kappa k_BT}{ze}\sinh\left(\frac{ze\psi_{CytC}}{2k_BT}\right)$$

$$\sqrt{\left[1+\frac{1}{\kappa R_{CytC}}\frac{2}{\cosh^2\left(\frac{ze\psi_{CytC}}{4k_BT}\right)}+\frac{1}{(\kappa R_{CytC})^2}\frac{8\ln\left[\cosh\left(\frac{ze\psi_{CytC}}{4k_BT}\right)\right]}{\sinh^2\left(\frac{ze\psi_{CytC}}{2k_BT}\right)}\right]}$$

$$Q_{CytC}=4\pi R_{CytC}^2*\sigma_{CytC}$$

Hydrophobic Interaction Energy

Hydrophobic interaction is represented by the single exponential function, $$\frac{F_{HB}}{R}=Ce^{\left(-\frac{x}{\lambda}\right)}$$

where C is the hydrophobic amplitude and λ (m) is the decay length. Integrating over x and substituting in the effective radius, hydrophobic interaction energy reflective is obtain for the interaction model:

$$V_{HB}=\frac{(R_{CdTe}+d)R_{CytC}}{R_{CdTe}+R_{CytC}+d}C\lambda e^{\left(-\frac{x}{\lambda}\right)}$$

The strength and the range of hydrophobic interaction have been previously shown to depend on the contact angle of the interacting substrates ($\theta_r$). Due to lack of literature data on the hydrophobicity of DMAET and CytC, data based on similar chemical moieties is used. The contact angle of 2-(diethyamino)ethanethiol (DEAET) on a gold coated substrate is found to be $\theta_c=74°$. Furthermore, interfacial reaction of polyimide film with ethanethiol induced reduction in polarity with water contact angle $64°<\theta_c<78°$. A self-assembled monolayer (SAM) of porphyrin on a gold substrate showed contact angle $76°<\theta_c<78°$. Based on the contact angle data, C=−9 (mN/m) and $\lambda$=2 (nm) are used, which are based on interacting surfaces with contact angle $\theta_c=81°$.

After addition of the other terms, including dipole-dipole, charge-dipole interactions, and hydrophobic interactions the pair potential becomes attractive for all separation distances. However, why such a pair potential does not lead to complete aggregation of the constituent species is further explored.

Self-limiting processes and therefore terminal assemblies appear because the system evolves toward an equilibrium state as can be seen in the temporal profile of electrokinetic potential ($\xi$) during the assembly. Starting from $\xi$=+26 mV and +7 mV corresponding to individual CdTe NPs and CytC, respectively (FIGS. 16A-16B), $\xi$ rapidly increases from +8 mV (0 h) to +48 mV within the first 5 hours. This state corresponds to the formation of large, dynamic, intermediate aggregates. Later, $\xi$ reduces slightly to +37 mV (10 h) and equilibrates at +31 mV (70 hours, FIG. 2F) due to the condensation of the intermediate aggregates. The $\xi$ values match the trend of SP diameters that peaked after about 1 hour of the assembly time (FIG. 10).

Two distinct coarse-grained models are developed to better understand 1) how the NP-CytC interaction prevents the DMAET-CdTe NPs from assembling into sheets, and 2) how the renormalized inter-SP charge-charge repulsion between NPs and CytC proteins during aggregation, as suggested by the potential (FIG. 2F), lead to the self-limiting assembly of SPs.

More specifically, molecular dynamics with a Langevin thermostat are used to simulate a model system of DMAET-CdTe NPs and CytC proteins at constant temperature and volume. Each constituent—NP or a protein molecule—is subject to conservative, random and drag forces $F_i^C$, $F_i^R$ and $F_i^D$, respectively. They can be essentially described as solid "beads" whose motion is governed by the Langevin equation:

$$m_i \ddot{r}_i = F_i^C + F_i^R + F_i^D.$$

Here $m_i$ and $r_i$ are the bead (unit) mass and position, respectively. The conservative force $F_i^C$ is determined by the gradient of the pairwise potentials between a bead and its neighbors. The random and drag forces represent the bombarding effects of solvent molecules on a bead. The random force $F_i^R$ is independent of the conservative force and satisfies the dissipation fluctuation theorem:

$$\langle F_i^R(t) \rangle = 0$$

$$\langle F_i^R(r), F_j^R(t') \rangle = 6\gamma k_B T \delta_{ij} \delta(t-t').$$

The drag force is related to the bead velocity $F_i^D=-\gamma v_i$, where $\gamma$ is the friction coefficient and $v_i$ is the bead velocity. A friction coefficient of $\gamma$=1.0 is selected to limit the ballistic motion of a bead in a time step to approximately $1.0\sigma$. The combination of the random and drag forces serves as a non-momentum-conserving thermostat for the system and helps to minimize numerical round-off errors that can accumulate during long simulation runs. Since the steady-state solution of the Langevin equation yields the Boltzmann velocity distribution, the equilibrated system is in the canonical ensemble, i.e., constant temperature and volume.

The computer simulations reveal details of the self-limiting mechanism of SP formation and elucidate the cooperative nature of multiparticle interactions and their universality as shown in FIGS. 17A-17C. Based on a coarse-grained model previously developed for CdTe NPs (FIG. 17A), the attractive non-covalent interactions between NPs and CytC are described by the empirical 12-6 Lennard-Jones potential. The Yukawa potential models the screened charge-charge, dipole-dipole, and dipole-charge interactions.

For the first model, CdTe NPs previously used in the work of Zhang et al., "Simulations and analysis of self-assembly of CdTe nanoparticles into wires and sheets," *Nano Lett.* 7, 1670-1675 (2007), incorporated herein by reference, are used. The NPs are modeled as 59 beads of diameter $1.0\sigma$ arranged into a truncated tetrahedron shape (FIG. 17A). The net positive charge ($\mu$ about +3e) is located at the NP center of mass and the dipole vector ($\mu$ about 100D) points from the center of mass to the bottom face (blue arrow, FIG. 17A). Meanwhile, CytC are modeled as spherical beads with a diameter of $d_{CytC}=4.0\sigma$. CytC units carry a charge of q about +3e and a dipole moment of $\mu$ about 340D. In the simulations, the charge and dipole moment values are specified in the corresponding reduced units defined as $q^*=q/(4\pi\epsilon_0\sigma\epsilon)^{1/2}$ and $\mu^*=\mu/(4\pi\epsilon_0\sigma^3\epsilon)^{1/2}$, respectively, where $\epsilon_0$ is the vacuum permittivity and e is the Lennard-Jones well depth (see below).

The Lennard-Jones 12-6 potential is used to model the face-to-face attraction between two NPs, in other words, between the constituent beads on the faces (yellow), and the interaction between NPs and CytC units. The LJ 12-6 interaction is truncated and shifted to zero at a distance of $2.5\sigma$. For the interaction between the NP and CytC units, the center-to-center distance is shifted by an amount $\Delta=(d_{bead}+d_{CytC})/2-d_{bead}=1.5\sigma$. The Lennard-Jones energy well depths, between NP-NP and between NP-CytC are varied from 0.01 $k_BT$ to 0.8 $k_BT$ to probe the conditions at which the NPs alone would assemble into sheets and those at which the NPs mix with CytC within the SPs. The other pairs (yellow-white and white-white) interact via the Weeks-Chandler-Andersen potential to mimic excluded volume (steric) interactions. The screened charge-charge, charge-dipole and dipole charge interactions between the NPs are localized to the NP centers of mass and are truncated at a distance of $5\sigma$.

The rotational degrees of freedom of tetrahedral NPs are incorporated using the equations for rotation of rigid bodies with quaternions. The velocity Verlet scheme is used to integrate the equation of motion with a time step $\Delta t=0.005\tau$. The natural units for these systems are the diameter of a bead, $\sigma$, the mass of a bead, m, and the Lennard-Jones well depth, a. The time scale is defined as $\tau=\sigma(ma)^{-1/2}$ and the dimensionless temperature is $T^*=k_BT/a$. The number density is defined as $\rho=N/V$, where N is the total number of particles and V is the box volume. The NPs and CytC are initialized randomly in the box and equilibrated under athermal conditions, i.e., all interactions are purely repulsive. After the mixing stage, the attraction between NPs and CytC is turned on and the simulation box is gradually compressed to $\rho\sigma^3$=0.2-0.3 to facilitate aggregation. The simulations are performed using HOOMD-Blue, and an in-house code.

FIGS. 17A-17C show the first-level coarse-graining model, wherein FIG. 17A is show truncated tetrahedral NPs with the dipole vector (blue) and attractive faces (yellow). FIG. 17B shows a two-dimensional sheet formed by NPs, while FIG. 17C shows spherical assemblies formed by a 1:1 mixture of 64 NPs and 64 CytC units. The NP faces and edges are drawn as smooth to better show the packing of the NPs within the sheet. Unlike in chains and sheets, the dipole moments of NPs and CytC within the spherical SPs do not exhibit any long-range correlation, indicated by a random orientation of their dipole moments (FIG. 17C, inset), presumably due to the strong screening effects and the flexible conformation of CytC.

Thus, using the first level coarse-grained model, it is observed that in the absence of CytC the truncated tetrahedral NPs assemble into a sheet (FIG. 17B). However, when mixed with CytC with a 1:1 molar ratio, the NPs and CytC form spherical aggregates (FIG. 17C) when the NP-CytC attraction, $a_{NP-CytC}$, is comparable to the NP-NP attraction, $a_{NP-NP}$. These results suggest that the sufficiently strong attraction between CytC proteins and CdTe NPs prevents the NPs from assembling into sheets and leads to the formation of bionic clusters.

Another model is developed to focus on the self-limiting assembly of the NPs and CytC proteins based on the observation that the NP shape and dipole moments are likely of little relevance to the process. In the second-level coarse-grained model, the DMAET-CdTe NPs and CytC are modeled as spherical beads with diameters of $1.0\sigma$ and $1.1\sigma$, respectively. The size ratio between the CytC and NPs is chosen to be smaller than in the experiment to take into account the flexible nature of the proteins at room temperature. Similar to the previous model, the NPs and CytC units interact via the Lennard-Jones 12-6 potential, screened charge-charge interaction, and dipole-dipole and charge-dipole interactions.

The screened charge-charge interaction between the NPs and CytC units is modeled by using the Yukawa potential:

$$U_{Yukawa}(r_{ij}) = A_{ij}\exp(-\kappa r_{ij})/(r_{ij}/\sigma),$$

where $r_{ij}$ is the distance between two units, $A_{ij}$ and $\kappa$ are the repulsion strength and inverse screening length, respectively. The repulsion strength between freely floating NPs and CytC is chosen as $A_{ij}=1.0\ k_BT/\sigma$ and the inverse screening length is chosen as $K=1.0\sigma^{-1}$, comparable with the diameter of the NPs and CytC units, as estimated in the previous section.

During the course of the simulation, the NPs and CytC are clustered into SPs based on their relative distances. A cutoff distance of $1.4\sigma$ is used to determine if two units (NPs or CytC) belong to the same SP. Unlike in previous studies, here the repulsion strength between units is treated as the same SP regardless of whether they are in the core or in the shell of the SP, because no attempt is made to characterize the local density of the NPs and CytC in the shell and the core of individual SPs. The repulsion strength between an NP (or a CytC) in an SP and either a NP or CytC external to the SP, $A_{inter}$, is linearly scaled by the SP volume to model the charge accumulation in the growing counterion layers covering the SPs. Specifically, for units from different SPs, the repulsion strength $A_{inter}$ is renormalized with the SP sizes:

$$A_{inter} = A_{ij} + (V_i + V_j - V^{(1)})s,$$

where $A_{ij}=1.0\ k_BT$ is the repulsion strength between two freely floating units, chosen as the baseline; $V_i$ and $V_j$ are the size of the SPs to which the interacting units belong; $V^{(1)}=\pi\sigma^3/6$ is the volume of a single-unit SP; and the slope s is an input parameter representing how rapidly the repulsion strength increases with the SP sizes. Essentially, s is the first derivative of $A_{inter}$ with respect to the SP sizes, and can be related to the slope of the ξ-potential during the early stage of assembly (FIG. 2F). To first order, $s=(A_{max}-A_{ij})/(V_{max}-V^{(1)})$ where $V_{max}$ is the terminal size of the SPs. The maximum value of the inter-SP repulsion strength, $A_{max}$, is determined such that no NP-CytC aggregation occurs at a given value of $\in_{NP-CytC}$. Physically, $A_{max}$ corresponds to the plateau region of the electrokinetic potential (FIG. 2F) when the SPs already acquire the terminal size. Specifically, for $\in_{NP-CytC}=5.0\ k_BT$, $A_{max}$ is found to be approximately $5.0\ k_BT/\sigma$. Because the number of units per SP is on the order of $10^4$, as estimated above, no attempt is made to match this number in the simulation mostly due to computational constraints. Instead, s is varied from $0.001\ k_BT/V^{(1)}$ to $0.1\ k_BT/V^{(1)}$ so that the SP terminal size would be in the range of 30-200 units. A smaller value of s would give a larger number of units per SP because that means $A_{inter}$ reaches $A_{max}$ at a higher value of $V_{max}$.

It is also important to note that because the inter-SP repulsion is due to the coexistence of the NPs and CytC, it is expected that s is dependent upon the molar ratio of the mixture. Specifically, s decreases with the volume fraction of the CytC because the SP size increases to infinity when the NPs dominate. In this model, for simplicity, it is assumed that s is inversely proportional to the NP/CytC molar ratio.

The inter-SP repulsion strength is renormalized as each SP assembles, so as to describe the structural adaptation of ionic clouds around NP and CytC during SP formation. As expected, simulated tetrahedrally-shaped DMAET-CdTe NPs on their own (in the absence of CytC) assembled into flat sheets (FIG. 17B). The presence of CytC dramatically alters their assembly pathway to produce hybrid NP-protein SPs when the attraction of CytC to the NPs is sufficiently strong. (FIG. 17C). To facilitate the computation while keeping essential physics of the self-limiting assemble process, NPs and proteins are modeled as spherical beads (FIGS. 4A-4E). This simplified model is useful to understand the control parameters for SP assembly and demonstrate generality of the assembly of NPs with proteins. Despite these simplifications, this model describes the experimental data remarkably well. The assembly of multiple SPs for a 1:1 ratio of components is observed, while deviations from this ratio produced irregular shapes (FIGS. 4D-4E).

Within SPs, NPs and CytC formed small clusters of a few particles (FIG. 4A) that correspond to domains about 6 nm in size, as observed from TEM (FIGS. 2A-2B). The simulated size distribution exhibits a pronounced peak (FIG. 4B) for the equilibrium state when the inter-SP repulsion balances the attraction between NPs and CytC. The small asphericity parameter (FIG. 4B, inset) indicates that most of the simulated aggregates are indeed spherical. Multiple SPs at their terminal size did not coalesce because the repulsion from their constituents to any approaching NP or protein exceeds the net attraction (FIGS. 18A-18D).

A time profile of the simulated self-assembly of SPs is shown in FIGS. 18A-18D. More specifically, FIG. 18A shows a snapshot of a 1:1 mixture having N=2000 NP and CytC units after $2000\tau$ equilibration at number density of $\rho=N/V=0.125\sigma^{-3}$. FIG. 18B shows system potential energy per unit upon compression from $0.001\sigma^{-3}$ to $0.125\sigma^{-3}$ followed by equilibration at $0.125\sigma^3$. FIG. 18C shows dependence of the number of structural units per SP, $(M_{SP})$, and FIG. 18D shows an average asphericity parameter $(A_S)$ of the SPs on the time of the assembly. Error bars in FIG. 18C are obtained from averaging over the SPs assembled in the system at the given time. The asphericity parameter $A_S$ characterizes the shape of the SP: $A_S=0$ corresponds to a perfectly spherical shape, $A_S=1$ corresponds to an infinitely long cylinder. The temporal profile of the potential energy plateaued for stable SPs indicating the trend toward an equilibrium state (FIG. 18B). When the SPs reach their terminal size, they become spherical in shape (FIGS. 18C-18D).

Using the second-level coarse-grained model with the renormalized inter-SP repulsion, the formation of uniform-sized SPs from binary mixtures of NPs and CytC with a 1:1 molar ratio is observed. The system potential energy converges within statistical error and the SP average size fluctuates around the same value from 5-10 independent runs with different number of NPs and CytC (N=2000-20000), different random seeds and different concentrations. FIGS. 18A-18D illustrate an example of the evolution of the number of units per SP and the SP asphericity parameter in one of the runs with a 1:1 mixture of 1000 NPs and 1000 CytC units. The results suggest that the system of uniform-sized SPs is stable and they become more spherical during the assembly. FIGS. 19A-19E show example snapshots for different average number of units per SP ($M_{SP}$) and number densities.

FIG. 19A-19E show simulation results of assembly of highly concentrated CdTe NPs and CytC. FIG. 19A shows a snapshot of a 1:1 mixture of NPs and CytC consisting of N=2000 units (NPs and CytC) in total in a cubic box with the size of L=20σ. The SPs are ordered into a face-centered cubic lattice. Each SP has $M_{SP}$=35 building blocks on average. In FIG. 19B, N=16000, L=40σ, $M_{SP}$=35; in FIG. 19C N=16000, L=50σ, $M_{SP}$=54; in FIG. 19D, N=13000, L=45σ, $M_{SP}$=80; and in FIG. 19E, N=13000, L=50σ, $M_{SP}$=118. The images are generated using the software VMD.

Continuous normalization of the charge screening conditions reflects the continuous change in the electric double layer for NPs as they assemble (FIGS. 20A-20C). FIGS. 20A-20C show an example of the time evolution of the system potential energy and average number of units per SP where the NP-CytC repulsion strength is not renormalized. Thus, FIGS. 20A-20C show simulation results without inter-SP charge-charge repulsion. The simulation involves a 1:1 mixture of NPs and CytC consisting of N=16000 units in total in a cubic box with the size of L=91σ when the inter-SP repulsion is not renormalized (FIG. 3C). FIG. 20A shows potential energy in the system, FIG. 20B shows an average number of building blocks in the system, and FIG. 20C shows SP size distribution.

In this case, the assembly is not limited and the SPs are not uniform in size. Thus, when the inter-SP charge-charge repulsion renormalization is excluded from the simulation model, the assembly is not self-limiting, leading to infinite aggregation and non-uniform SPs (FIGS. 4C, 20A-20C) in disagreement with the experiments.

The effects of important media factors such as ionic strength and temperature on the size of the terminal SPs are also captured qualitatively in the simulation model. As the salt concentration increases, the screening length of the electrostatic repulsion decreases, leading to the reduction in the effective repulsion between freely floating NPs and CytC. As a result, the number of NPs and CytC within the terminal SPs should increase so as to accumulate sufficient inter-SP repulsion to balance with the net attraction between individual units. The decrease in the SP terminal size with the increased NaCl concentration (FIG. 3E) is qualitatively recovered in the simulation model (FIG. 3E, inset). The agreement between experimental and simulation data is pronounced when the two data sets are fit with decaying laws and plotted using dimensionless axes (in FIG. 3F, showing dimensionless inverse screening length (κ) and SP diameter (D*)).

To compare qualitatively simulation and experimental data (FIG. 3E), the data sets are fit with the decay laws f(x)=A exp[-(x-B)/C]+D, where A, B, C and D are fitting parameters; x is either the NaCl concentration in experiment or the inverse screening length in simulation.

The obtained parameters are then used to rescale the data points accordingly. For instance, for the experimental curve (FIG. 3D), given the obtained parameter set of (A1, B1, C1, and D1) the NaCl concentrations are rescaled as ([NaCl]–B1)/C1. Likewise, the inverse screening lengths are rescaled as (κ–B2)/C2. The same notation κ* is used for the x axis of the plot in FIG. 3D, because the inverse screening length increases monotonously with the NaCl concentration in the conditions under investigation. The y axis of the plot in FIG. 3D is obtained by rescaling the SP diameters by ($D_{SP}$–D)/A. D* denotes the dimensionless SP diameters in both experiment and simulation.

Meanwhile, the temperature dependence of the SP terminal size is consistent with experimental data in the lower temperature regime where $k_B T/\in$ about 1.0 (FIG. 3G). In this temperature range, the net effective attraction between NPs and CytC is comparable to thermal fluctuations and the terminal SP size is fairly insensitive to temperature. For $k_B T/\in$ much greater than 1.0, the attraction strength becomes weaker than thermal fluctuations, and simulation results diverge from experimental observation with the decrease in the SP terminal size (FIG. 3G, inset). This divergence can be attributed to the change in the conformation of CytC that invalidates the Lennard-Jones model in use.

Forming supraparticle terminal assemblies is a relatively straightforward method of making complex inorganic and biological nanosystems from a variety of components. A second new redox enzyme, namely nitrate reductase (NRed), is incorporated as an additional component in SPs as they are assembled with CytC and NPs. NRed integration into SPs led to the increase of SP size and decrease of ξ-potential (FIGS. 21A-21E). The positions of all peaks in the UV-Vis/CD spectra remained unchanged, indicating that the electronic state and conformation of the CytC in the SPs are preserved (FIGS. 21F-21G). Various spectroscopy data indicate that 25±8 NRed are incorporated in SPs; the number of enzyme molecules matches well with the observed increase of SP diameter (FIGS. 21C-21E).

EXAMPLE 2

Nicotinamide adenine dinucleotide phosphate, (NADPH) is added to the SP dispersion to serve as a sacrificial electron donor. The SPs are prepared with CytC (20 μL; 300 μM), CdTe NPs (dispersion—1 mL) are left at temperature 4° C., 20° C., 35° C., 55° C. and 70° C. during three days. NADPH (10 μl) is added to the SPs dispersion which are examined in the transmission electronic microscopy after be diluted (100 times). Incorporation of NADPH in the SPs is observed based on EDX data (FIG. 21H). Direct reduction of $NO_3^-$ by NADPH cannot occur and must have been catalyzed by NRed.

Nitrate reduction assay: Prior to the assay, each of 500 μL of diluted samples is mixed with 50 μL of 2,3-diaminon-aphthalene (DAN) and 100 μL of 2.8M-NaOH solution (Cayman Chemical). Fluorescence emission at 417 nm of the samples is recorded by exciting the samples at 375 nm (Synergy2 plate reader, Biotek). The activity is measured by a standard fluorescence assay method to quantify produced $NO_2^-$ (μmol/g-enzyme)². The concentration of $NO_2^-$ is determined by a standard plot of different concentrations of $NO_2^-$ (FIG. 6).

Whether this catalytic process can be driven by light adsorption into CdTe is further explored. Since the direct electron transfer from CdTe to NRed is also impeded, it has to be mediated by CytC. Enzymatic Reduction of Nitrate occurs as follows: 10 μL of enzyme, NRed, solution (Cayman Chemical) is added to 770 μL of the aqueous solution containing CdTe/CytC SP (40 μL), cofactor (NADPH, 10 μL, Cayman Chemical), and $NaNO_3$ (150 μL, 200 mM). The solution is placed in a 800 μL quartz cuvette (Starna cells) and illuminated at 470 nm via Horiba FluoroMax®-3 monochromator for 1 hour with slit width for excitation at 20 nm. The wavelength matches to the onset of excitonic absorption of CdTe NPs in the bionic SPs. During illumination, 30 μL of aliquots is diluted with 470 μL of water at desired time intervals are taken for analysis.

The rate of $NO_2^-$ production by SP-NRed in presence of NADPH increases four-fold when illuminating the SP at 470 nm—the absorption peak of CdTe NPs (FIG. 5A). This indicates that the sequence of electron transfer reactions NADPH→CdTe (hv)→CytC→NRed→$NO_3^-$ is believed to take place. The existence of CytC in the reduced form in SPs facilitates the electron transfer to NRed, which in turn reduces $NO_3^-$ to $NO_2^-$. After that, the photo-excited electrons from CdTe NPs are continuously supplied to CytC, which shuttles them to NRed. The holes in CdTe are eliminated by NADPH. Dense packing of all the organic and inorganic building blocks within SPs and the large interfacial area of the bicontinuous percolated structure of SPs facilitated all the electron transfer reactions. The importance of dense packing could also be seen for clusters of inorganic catalysts. Side reactions, such as reduction of NP holes by oxidizable residues on the proteins, e.g. tyrosine, in CytC, are highly probable, similarly to bioconjugates.

FIG. 22 is a scanning electron microscopy image of SP-NRed in presence of NADPH. No change in spherical morphology compared to original 1:1 CdTe/CytC SPs is observed. Scale bar is 500 nm. FIG. 23 shows a plot of electrokinetic ξ-potential of SP-NRed in presence of NADPH measured in the course of the photoenzymatic reaction.

In the absence of light, the presence of SPs had virtually no effect on the activity of the enzyme (FIG. 5A). Control experiments confirm the significance of the NPs and SPs for the photoenzymatic $NO_3^-$ reduction. These include the enzyme reaction (i) either with CdTe NPs or (ii) with CytC upon illumination (FIG. 4A, inset). None of the control experiments show enzyme activity as high as for illuminated SP-NRed in presence of NADPH.

Figures 5C, 5D:
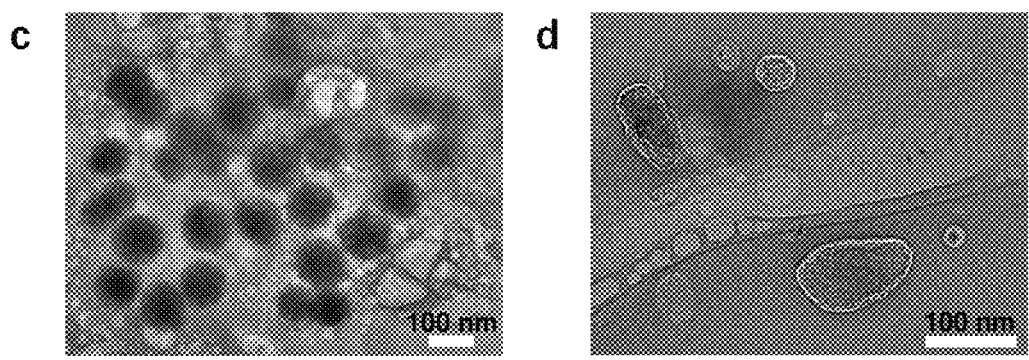

The assembled SPs remain intact after 20 min of photoreaction. However, the disassembly of SP-NRed occurred after about 30 min of SP-NRed's exposure to light (FIGS. 5C-5D), which is synchronized with the drop in photoenzymatic activity (FIGS. 5A, 22). The decrease of activity is attributed to irreversible oxidation of NPs by photogenerated holes. This results in removal of DMAET ligands from the surface of NPs, and therefore the loss of attractive intermolecular interactions. The synchronization of the drop in enzymatic reduction and onset of disassembly vividly demonstrates that the formation of SPs is necessary to obtain higher photoenzymatic activity. TEM images support this conclusion (FIG. 5D).

In summary, CdTe NPs and like-charged proteins self-organize into self-limiting spheres following a pattern previously unseen for the individual components. These superstructures display complex internal organization and can incorporate multiple biological components. The protein component retains its functionality and moreover permitting integration of the light absorbing properties of the NPs and catalytic properties of the enzyme. Because only simple omnipresent forces are involved on formation of SPs, it is contemplated and expected that supraparticle nanoassemblies can be made from a large variety of NPs and proteins. The simplicity of their preparation is conducive to a large variety of potential applications.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A supraparticle comprising:
   a nanoparticle species having a surface with a first charge and an average particle size diameter of greater than or equal to about 1 nm to less than or equal to about 100 nm; and
   a protein species having a second charge that is the same as the first charge, wherein the nanoparticle species and the protein species are self-assembled together via intermolecular forces without any intramolecular chemical bonding to form the supraparticle having a ξ-potential of greater than or equal to about +30 mV.

2. The supraparticle of claim 1, wherein the nanoparticle species is selected from the group consisting of: gold (Au), silver (Ag), copper (Cu), nickel (Ni), iron (Fe), carbon (C), platinum (Pt), silicon (Si), cadmium (Cd), cadmium telluride (CdTe), cadmium selenide (CdSe), cadmium sulfide (CdS), mercury tellurium (HgTe), mercury selenide (HgSe), mercury sulfide (HgS), lead telluride (PbTe), lead selenide (PbSe), lead sulfide (PbS), molybdenum sulfide ($MoS_2$), iron (II) sulfide ($FeS_2$), iron sulfide (FeS), iron selenide (FeSe), zinc oxide (ZnO), and combinations thereof.

3. The supraparticle of claim 1, wherein the nanoparticle species comprises a semiconductive material selected from the group consisting of: Cd, CdS, CdSe, CdTe, Si, and combinations thereof.

4. The supraparticle of claim 1, wherein the nanoparticle species comprises CdTe or $FeS_2$.

5. The supraparticle of claim 1, wherein the surface of the nanoparticle species comprises at least one stabilizer having the first charge.

6. The supraparticle of claim 5, wherein the at least one stabilizer comprises 2-(dimethylamino)ethanethiol (DMAET).

7. The supraparticle of claim 6, wherein the nanoparticle species comprises CdTe, forming a DMAET-stabilized CdTe.

8. The supraparticle of claim 1, wherein the protein species comprises an enzyme.

9. The supraparticle of claim 8, wherein the enzyme retains at least 90% of catalytic capability when incorporated into the supraparticle as compared to catalytic capability of the enzyme in a free state.

10. The supraparticle of claim 1, wherein the supraparticle further comprises a biomolecule.

11. The supraparticle of claim 1, wherein the first charge and the second charge are positive.

12. The supraparticle of claim 1, wherein a ratio of the nanoparticle species to the protein species in the supraparticle is about 10:1 to about 1:10.

13. The supraparticle of claim 12, wherein the ratio of the nanoparticle species to the protein species in the supraparticle is about 1.5:1 to about 1:1.5.

14. The supraparticle of claim 1, having an average particle size diameter of greater than or equal to about 50 nm to less than or equal to about 200 nm.

15. A supraparticle comprising:
   a nanoparticle species having a surface with a first charge and an average particle size diameter of greater than or equal to about 1 nm to less than or equal to about 100 nm; and
   a protein species having a second charge that is the same as the first charge, the protein species comprising an enzyme, wherein the nanoparticle species and the protein species are self-assembled together via intermolecular forces without any intramolecular chemical bonding to form the supraparticle having a substantially round shape and a ζ-potential of greater than or equal to about 30 mV, wherein the enzyme retains at least 90% of catalytic capability when incorporated into the supraparticle as compared to catalytic capability of the enzyme in a free state.

16. A photoreactive supraparticle comprising:
   a nanoparticle species having a surface with a first charge and an average particle size diameter of greater than or equal to about 1 nm to less than or equal to about 100 nm, wherein the nanoparticle species is reactive to electromagnetic radiation and comprises a material selected from the group consisting of: Cd, CdS, CdSe, CdTe, Si, $FeS_2$, and combinations thereof; and
   a protein species having a second charge that is the same as the first charge, wherein the nanoparticle species and the protein species are assembled together without any intramolecular chemical bonding to form the supraparticle, wherein in the presence of the electromagnetic radiation, the protein species in the supraparticle has a reactivity that is at least 100% greater than a comparative reactivity of the protein species in the absence of the electromagnetic radiation.

17. The supraparticle of claim 16, wherein the nanoparticle species comprises CdTe or $FeS_2$.

\* \* \* \* \*